(12) United States Patent
Broude et al.

(10) Patent No.: US 10,913,983 B2
(45) Date of Patent: Feb. 9, 2021

(54) SENSITIVITY MARKERS AND USES FOR CDK7 INHIBITORS IN BREAST CANCERS

(71) Applicant: UNIVERSITY OF SOUTH CAROLINA, Columbia, SC (US)

(72) Inventors: Eugenia Broude, Lexington, SC (US); Martina McDermott, Columbia, SC (US)

(73) Assignee: University of South Carolina, Columbia, SC (US)

(*) Notice: Subject to any disclaimer, the term of this patent is extended or adjusted under 35 U.S.C. 154(b) by 23 days.

(21) Appl. No.: 16/038,283

(22) Filed: Jul. 18, 2018

(65) Prior Publication Data
US 2019/0024182 A1 Jan. 24, 2019

Related U.S. Application Data

(60) Provisional application No. 62/533,701, filed on Jul. 18, 2017.

(51) Int. Cl.
A61K 31/51 (2006.01)
G01N 33/68 (2006.01)
C12Q 1/6886 (2018.01)
A61K 31/517 (2006.01)
A61K 31/506 (2006.01)
G01N 33/574 (2006.01)
A61K 31/519 (2006.01)

(52) U.S. Cl.
CPC .......... C12Q 1/6886 (2013.01); A61K 31/506 (2013.01); A61K 31/517 (2013.01); A61K 31/519 (2013.01); G01N 33/57415 (2013.01); G01N 33/6872 (2013.01); C12Q 2600/106 (2013.01); C12Q 2600/158 (2013.01); G01N 2333/4706 (2013.01)

(58) Field of Classification Search
CPC combination set(s) only.
See application file for complete search history.

(56) References Cited

U.S. PATENT DOCUMENTS

| | | | |
|---|---|---|---|
| 5,994,055 A | 11/1999 | Cujec et al. | |
| 2016/0122323 A1 | 5/2016 | Gray et al. | |
| 2017/0174692 A1 | 6/2017 | Marineau et al. | |
| 2017/0327496 A1 | 11/2017 | Ciblat et al. | |
| 2018/0169097 A1* | 6/2018 | Hammerman | A61K 31/506 |
| 2018/0208578 A1 | 7/2018 | Ciblat et al. | |

FOREIGN PATENT DOCUMENTS

| | | |
|---|---|---|
| CA | 2972239 | 6/2016 |
| CN | 105849099 | 8/2016 |
| WO | WO 2014/063068 | 4/2014 |
| WO | WO 2015/058140 | 4/2015 |
| WO | WO 2015/058163 | 4/2015 |
| WO | WO 2015/154039 | 10/2015 |
| WO | WO 2016/105528 | 6/2016 |
| WO | WO 2016/201370 | 12/2016 |
| WO | WO2016201370 | * 12/2016 |
| WO | WO 2017/160797 | 9/2017 |
| WO | WO 2018/013867 | 1/2018 |

OTHER PUBLICATIONS

Guix et al, J Clin Onco 26:897-906, 2008 (Year: 2008).*
Wang et al Cell 163:174-186, 2015 (Year: 2015).*
Ali, et al. "The development of a selective cyclin-dependent kinase inhibitor that shows antitumor activity," Cancer Res. 69(15), (2009), pp. 6208-6215.
Berry, et al. "Regulation of FOXC1 stability and transcriptional activity by an epidermal growth factor-activated mitogen-activated protein kinase signaling cascade," J Biol Chem 281(15), (2006), pp. 10098-10104.
Bhattacharya, et al. "Functional role of p35srj, a novel p300/CBP binding protein, during transactivation by HIF-1." Genes Dev 13(1)(1999), pp. 64-75.
Cayrol, et al. "THZ1 targeting CDK7 suppresses STAT transcriptional activity and sensitizes T-cell lymphomas to BCL2 inhibitors," Nat Commun 8, (2017), p. 14290.
Chipumuro, et al. "CDK7 inhibition suppresses super-enhancer-linked oncogenic transcription in MYCN-driven cancer," Cell 159(5), (2014), pp. 1126-1139.
Chou, et al. "CITED2 functions as a molecular switch of cytokine-induced proliferation and quiescence," Cell Death Differ 19(12), (2012), pp. 2015-2028.
Chou TC. "Drug combination studies and their synergy quantification using the chou-talalay method," Cancer Res 70(2), (2010), pp. 440-446.
Chou, et al. "Cited2 modulates TGF-beta-mediated upregulation of MMP9," Oncogene 25(40), (2006), pp. 5547-5560.
Christensen, et al. "Targeting transcriptional addictions in small cell lung cancer with covalent CDK7 inhibitor," Cancer Cell 26(6), (2014), pp. 909-922.
Fang, et al. "A new tumour suppression mechanism by p27Kip1: EGFR down-regulation mediated by JNK/c-jun pathway inhibition," Biochem J 463(3), (2014), pp, 383-392.
Fisher RP. "The CDK network: Linking cycles of cell division and gene expression," Genes Cancer 3(11-12), (2012), pp. 731-738.
Greenall, et al. "Cyclic-dependent kinase 7 is a therapeutic target in high-grade glioma," Oncogenesis 6(5), (2017), p. e336.

(Continued)

Primary Examiner — Lei Yao
(74) Attorney, Agent, or Firm — Dority & Manning, P.A.

(57) ABSTRACT

Disclosed are targeted anti-proliferative approaches for breast cancer utilizing CDK7 inhibitors having efficacy in multiple subtypes of breast cancer, including but without limitation to ER-positive, HER2-positive and Triple Negative Breast Cancer. Methods utilize CDK7 inhibitors alone as well in conjunction with EGFR inhibitors, which provides synergistic anti-proliferative effects on breast cancer cells across a broad spectrum of breast cancer subtypes. Methods for determining sensitivity of breast cancer subtypes to CDK7 inhibitors based upon CITED2 expression levels are also described.

9 Claims, 20 Drawing Sheets
Specification includes a Sequence Listing.

(56) References Cited

OTHER PUBLICATIONS

Gyorffy, et al. "An online survival analysis tool to rapidly assess the effect of 22,277 genes on breast cancer prognosis using microarray data of 1,809 patients," *Breast Cancer Res Treat* 123(3), (2010), pp. 725-731.
Harrod, et al. "Genomic modelling of the ESR1 Y537S mutation for evaluating function and new therapeutic approaches for metastatic breast cancer," *Oncogene* 36(16), (2017), pp. 2286-2296.
Held, et al. "Ligand binding promotes CDK-dependent phosphorylation of ER-alpha of serine 294 but inhibits ligant-independent phosphoylation of serine 305," *Mol Cancer Res* 10(8), (2012), pp. 1120-1132.
Jayaraman, et al. "CITED2 modulated breast cancer metastatic ability through effects on IKKalpha," *Mol Cancer Res* 14(8), (2016), pp. 730-739.
Jiang, et al. "Targeting super-enhancer-associated oncogenes in oesophageal squamous carcinoma," *Gut* (2016).
Kelso, et al. "Cycliti-dependent kinase 7 controls mRNA synthesis by affecting stability of preinitiation complexes, leading to altered gene expression, cell cycle progression, and survival of tumor cells," *Mol Cell Biol* 34(19), (2014), pp. 3675-3688.
Kwiatkowski, et al. "Targeting transcription regulation in cancer with a covalent CDK7 inhibitor," *Nature* 511(7511), (2014), pp. 616-620.
Larochelle,"Cyclin-dependent kinase control of the initiation-to-elongation switch of RNA polymerase II," *Nat Struct Mol Biol* 19(11), (2012), pp. 1108-1115.
Lau, et al. "CITED2 modulates estrogen receptor transcriptional activity in breast cancer cells," *Biochem Biophys Res Commun* 437(2), (2013), pp. 261-266.
Lau, et al. "Identification of prospective factors promoting osteotropism in breast cancer: A potential role for CITED2," *Int J Cancer* 126(4), (2010), pp. 876-884.
Levin ER. "Bidirectional signaling between the estrogen receptor and the epidermal growth factor receptor," *Mol Endocrinol* 17(3), (2013), pp. 309-317.
Li, et al. "Therapeutic rationale to target highly expressed Cdk7 conferring poor outcomes in triple-negative breast cancer," *Cancer Res* (2017).
Li, et al. "Hormonal induction of polo-like kinases (plks) and impact of Plk2 on cell cycle progression in the rat ovary," *PLoS One* 7(8), (2012), p. e41844.
Lolli, et al. "CAK-cyclin-dependent activating kinase: A key kinase in cell cycle control and a target for drugs?" *Cell Cycle* 4(4), (2005), pp. 572-577.
McDermott, et al. "Inhibition of CDK8 mediator kinase suprresses estrogen dependent transcription and the growth of estrogen receptor positive breast cancer," *Oncotarget* (2017).
Minemura, et al. "CITED2 in breast carcinoma as potent prognostic predictor associated with proliferation, migration and chemoresistance," *Cancer Sci* 107(12), (2016), pp. 1898-1908.
Morales, et al. "Overview of CDK9 as a target in cancer research," *Cell Cycle* 15(4), (2016), pp. 519-527.
Obaya et al. "The proto-oncogene c-myc acts through the cyclin-dependent kinase (cdk) inhibitor p27(Kip1) to facilitate the activation of Cdk4/6 and early G(1) phase progression," *J Biol Chem* 277(34), (2002), pp. 31263-31269.
Patel, et al. "Expression of CDK7, cyclin H, and MAT1 is elevated in breast cancer and is prognostic in estrogen receptor-positive breast cancer," *Clin Cancer Res* 22(23), (2016), pp. 5929-5938.
Ran, et al. "Induction of c-fos and c-myc mRNA by epidermal growth factor or calcium ionophore is cAMP dependent," *Proc Natl Acad Sci USA* 83(21), (1986), pp. 8216-8220.
Roeder, RG. "Transcriptional regulation and the role of diverse coactivators in animal cells," *FEBS Lett* 579(4), (2005), pp. 909-915.
Wang, et al. "CDK7-dependent transcriptional addiction in triple-negative breast cancer," *Cell* 163(1), (2015), pp. 174-186.
Whittaker, et al. "Inhibitors of cyclin-dependent kinases as cancer therapeutics," *Pharmacol Ther* 173, (2017), pp. 83-105.
Yahata, et al. "Selective coactivation of estrogen-dependent transcription by CITED1 CBP/p300-binding protein," *Genes Dev* 15(19), (2001), pp. 2598-2612.
Zhang, et al. "Preclinical efficacy and molecular mechanism of targeting CDK7-dependent transcriptional addiction in ovarian cancer," *Mol Cancer Ther* (2017).

* cited by examiner

Luminal A

Luminal B

Basal

HER 2+

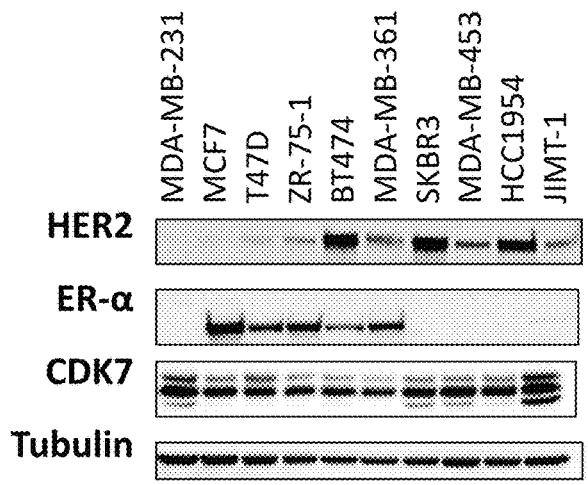
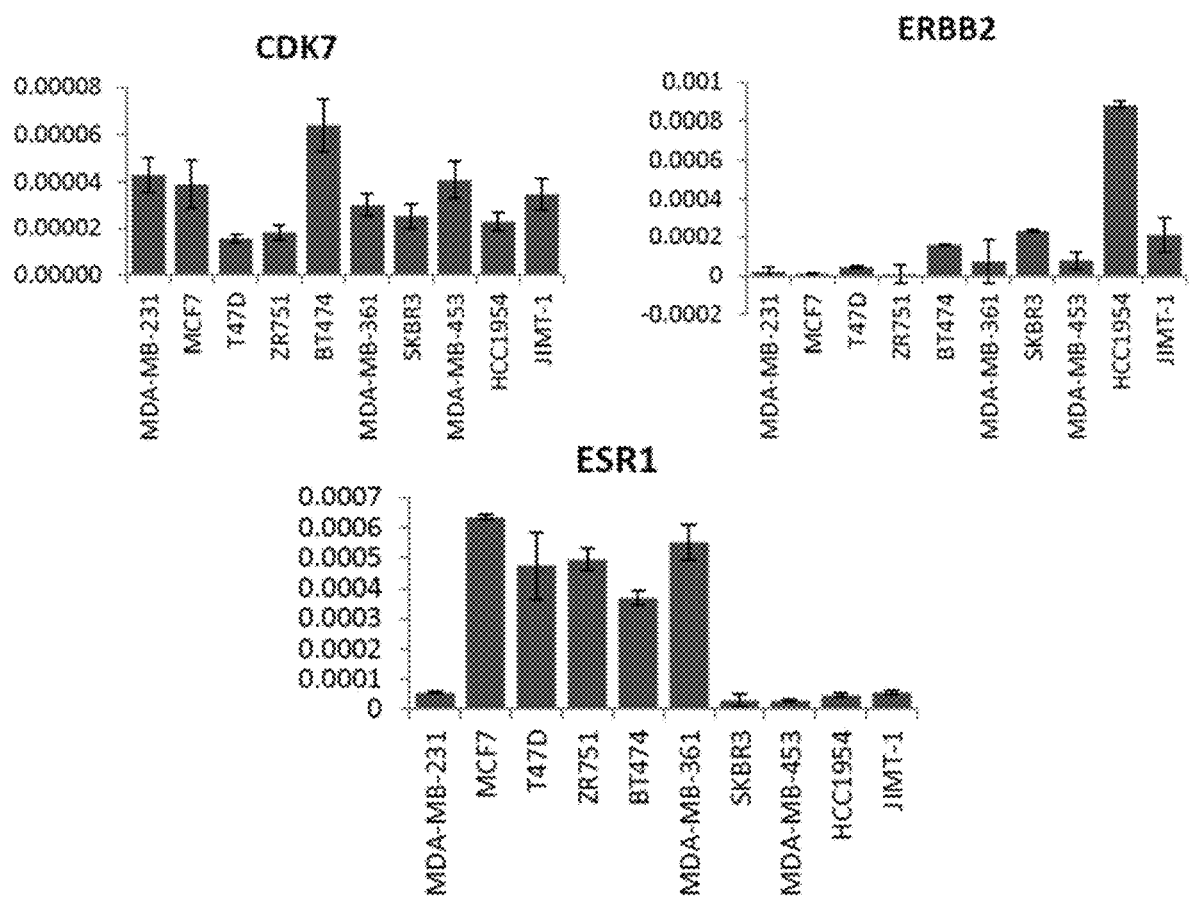
FIG. 3A
FIG. 3B

CDK7 expression

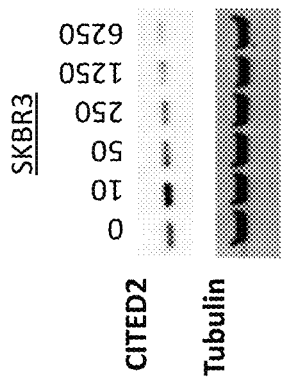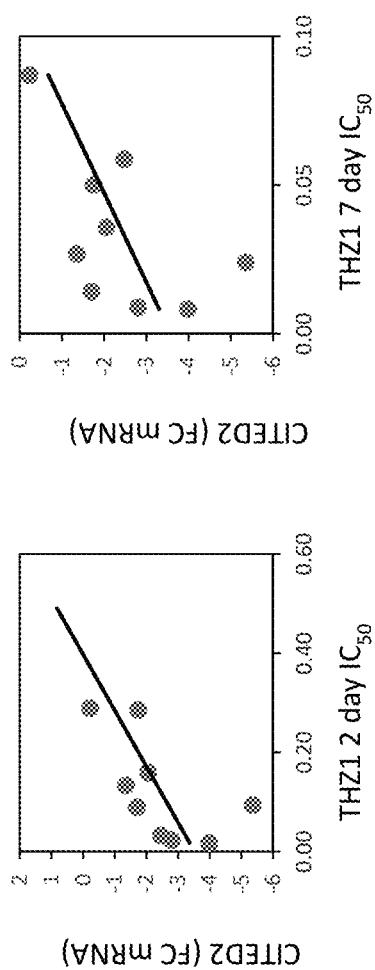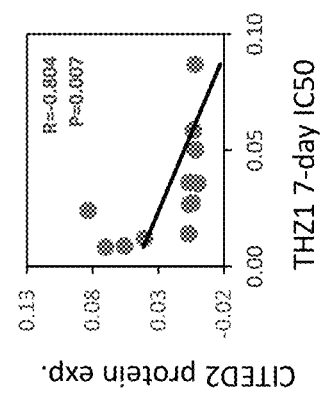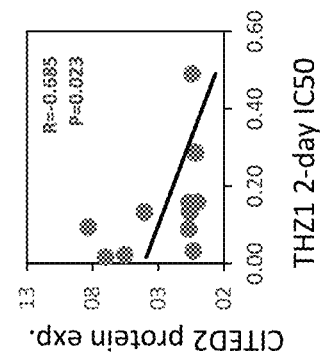
FIG. 6C
FIG. 6D
FIG. 6E

SEQUENCE LISTING

<160> NUMBER OF SEQ ID NOS: 42

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgagaacatg gtaatgggga gg                                               22

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acagtgctct gccctaagtt                                                  20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caggatctct agccaggcac                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atgatcaact gggcgaagag                                                  20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggttccttcc cctaatgggt c                                                21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6 caccccccaaa ggcaaaaacg                                                 20

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccaacaggaa ctatgacctc gactac                                           26

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctcgaatttc ttccagatat cct                                              23

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttgcggcgta gactttgtta                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agatctcgcg gattatcgtc                                                  20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
catatggtct gccatttcca                                                  20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaggtcccct ctatgtgctg                                                  20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctgaccaaaa tcatctgtgc cc                                              22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgtggcttcg tctcggaatt                                                 20

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acagaagaaa atgtttcaga cggt                                            24

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cttctgaggc caggcttctt                                                 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggagaaaccg aggttggagg                                                 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggagatagct tgtccggtgg                                                 20

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caccacaagt cccagtaggg                                              20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggaaccgaca tttgttgggc                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tcaagcagat tgtctccgcc                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caaaaggcca caggagaagc                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggtggggatg gttggatctg                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aaccctggta cataggccac                                              20

<210> SEQ ID NO 25
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aaggggcagc gtcacataaa                                                 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
actacaaccc gctcatgtcg                                                 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ttacagaggg ctgcacgatg                                                 20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gtcgtggctg tcacaagtct                                                 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccacctgtgg gagttcatcc                                                 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
catgtccggc tgtatcgtga                                                 20

<210> SEQ ID NO 31
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gcgtgggttt tctccgtaca                                                   20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctcagacagc cgtgaaaagc                                                   20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
accgcgacat taaggacgaa                                                   20

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gcgctcaccg tcgaagt                                                      17

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ctgtcctcac gggggttatc                                                   20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tcaaggactc aggcttggaa                                                   20

<210> SEQ ID NO 37
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 37
ttcctactgt cttctccttc gt                                              22

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
atccggcaag acagaccttc                                                 20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cggtgaaagc ttggggactt                                                 20

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ttggggacta tcaccacttg c                                               21

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aaatttgggg tggaaaggtt                                                 20

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tcctgatttc tgcagctctg t                                               21
```

SENSITIVITY MARKERS AND USES FOR CDK7 INHIBITORS IN BREAST CANCERS

FEDERAL RESEARCH STATEMENT

This invention was made with Government support under Grant Nos. NIH P20 GM109091 and NIH 30 GM103336, awarded by National Institutes of Health. The Government has certain rights in the invention.

This invention was made with Government support under Grant No. NIH P20 GM109091, awarded by National Institutes of Health. The Government has certain rights in the invention.

SEQUENCE LISTING

The instant application contains a Sequence Listing which has been filed electronically in ASCII format and is hereby incorporated by reference in its entirety. Said ASCII copy, created on Aug. 16, 2018, is named USC-578_(1288)_SL.txt and is 9,794 bytes in size.

BACKGROUND

In recent years, the advent of targeted therapies for estrogen receptor (ER) positive and HER2 positive breast cancer has significantly improved the outcome for breast cancer patients. However, lack of response and high rates of relapse following treatment are significant clinical issues in the management of breast cancer. In addition, there is a distinct lack of targeted therapies and treatment options for triple negative breast cancer (TNBC).

A strategy currently under investigation in cancer treatment involves targeting transcriptional regulation via inhibition of a subclass of cyclin dependent kinases that are involved primarily in transcription rather than cell cycle progression. Phosphorylation of serines in the heptapeptide repeat comprising the carboxy-terminal domain of RNA polymerase II (RNA Pol II) is an essential step for efficient transcription. Cyclin dependent kinase 7 (CDK7) functions as part of the TFIIH complex to phosphorylate RNA Pol II at Ser5 and Ser7 during initiation and promoter clearance, allowing the elongation complex to move downstream from the transcriptional start site. In addition to regulating transcription, CDK7 promotes cell cycle progression by acting as a CDK-activating kinase (CAK) in a trimeric complex with Cyclin H and MAT, phosphorylating cell cycle CDKs such as CDK1 and CDK2. Thus, CDK7 has been examined as a target in cancer treatment.

Interest in targeting CDK7 in cancer treatment has been boosted by development of the potent covalent inhibitor THZ1. THZ1 has shown promising results in preclinical studies on T-cell leukemia, neuroblastoma, small cell lung cancer, glioma and ovarian cancer. CDK7 has also been identified as a promising therapeutic target in TNBC, which was reported to be uniquely sensitive to CDK7 inhibition among the principal molecular subtypes of breast cancer.

Through studies utilizing CRISPR-Cas9-mediated knockout of CDK7 and THZ1 and by comparing the responses of TNBC and ER-positive breast cancers, TNBC was reported to be exquisitely dependent on CDK7, in contrast to ER-positive breast cancers. This unique dependence has been ascribed to an "Achilles cluster" of TNBC-specific critical genes regulated by super-enhancers requiring CDK7. THZ1 has been shown to induce apoptosis in TNBC cell lines in vitro and to inhibit the growth of xenograft and patient-derived xenograft models of TNBC in vivo.

CDK7 expression and activity have not been examined in HER2 positive breast cancer. Moreover, a clearer understanding of the effect of CDK7 inhibition in multiple cancer cell subtypes, including TNBC subtypes, has not been obtained. Such understanding could lead to methods for treating a broad spectrum of breast cancer types through CDK7 inhibition.

SUMMARY

In general, disclosed are methods for decreasing proliferation of breast cancer cells. Beneficially, the methods are applicable to a broad spectrum of breast cancer subtypes, including TNBC, HER2 positive, and ER positive breast cancers and are applicable to in vivo treatment and diagnostic methods as well as in vitro applications.

In one embodiment, a method can include testing a sample of breast cancer cells for basal expression level of CITED2 (CBP/300-interacting transactivator with Glu/Asp-rich carboxy-terminal domain-2). A relatively high basal expression level of CITED2 as compared to a control expression level can identify the breast cancer cells as being sensitive to CDK7 inhibitors. For example, the basal expression level of the cancer cells can be about 1.5 times or more higher than the expression level of a cancer cell line known to be resistant to treatment with CDK7 inhibitor. Upon determination that the breast cancer cells are sensitive to CDK7 inhibitors, the method can further include delivering a CDK7 inhibitor (e.g., THZ1 or BS-181) to the breast cancer cells, upon which, proliferation of the breast cancer cells can be decreased.

According to another embodiment, a method for decreasing proliferation of breast cancer cells is disclosed that includes delivering to a sample of breast cancer cells a CDK7 inhibitor (e.g., THZ1 or BS-181) and an EGFR inhibitor (e.g., erlotinib). As described further herein, it has been discovered that combination of a CDK7 inhibitor and an EGFR inhibitor has a synergistic effect, believed to be via inhibition of CDK7-mediated transcription that in turn the potentiates the detrimental effects of EGFR inhibition on the sample of breast cancer cells.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 3A illustrates immunoblotting results for ER-α, HER2 and CDK7 basal expression in a variety of breast cancer cell lines.

FIG. 3B shows the mRNA analysis (Q-PCR, relative expression to a control) of CDK7 protein (top left), HER2 (ERBB2) protein (top right) and ERα (ESR1) protein (bottom) in a panel of cell lines representing multiple subtypes of breast cancer.

FIG. 6C shows bi-variant scattergraph and Spearman rank correlation showing fold change (FC) in mRNA expression levels of CITED2 vs. IC50 at day 2 (left) and day 7 (right) following treatment with THZ1.

FIG. 6D illustrates immunoblotting results after cells were treated with a vehicle control (0) or increasing concentrations of THZ1 (10-6250 nM) for 4 hours, where immunoblotting was performed for CITED2 with α-tubulin as a loading control.

FIG. 6E illustrates an immunoblotting analysis of basal CITED2 protein levels in cell line panels shown with α-tubulin as a loading control (right) and also shows a bi-variant scattergraph and Spearman rank correlation for basal CITED2 protein expression vs. IC50 at 2 days (center) and at 7 days (right) following treatment with THZ1.

Figure 1A:
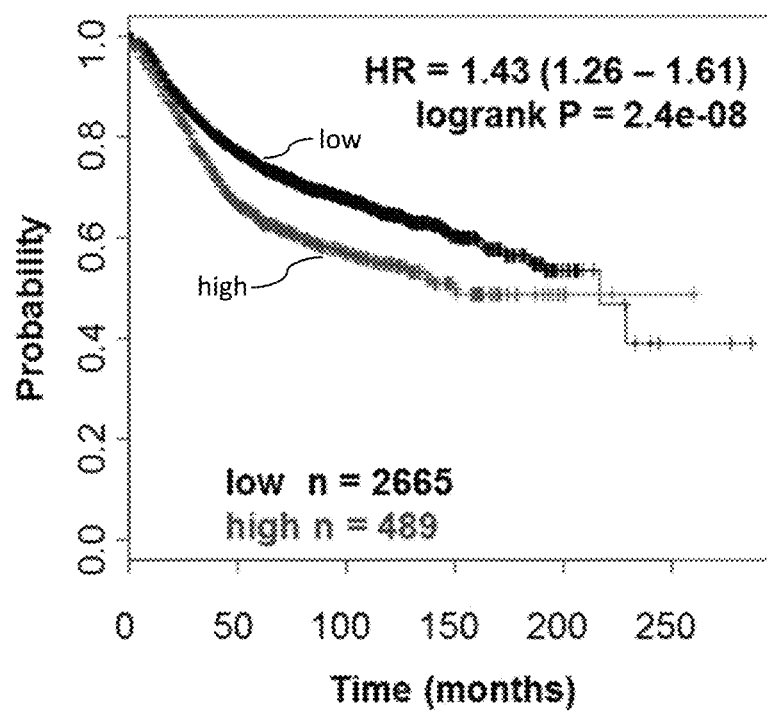
FIG. 1A, illustrates the CDK7 expression data from 3,951 breast cancer patient tumor samples. The association of CDK7 expression with Relapse Free Survival (RFS) in the microarray data is shown. Data was determined using the KM-plotter online survival analysis tool.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, disclosed herein are methods for treating a broad spectrum of breast cancers through inhibition of CDK7. Disclosed methods have been discovered through exploration of the therapeutic potential of CDK7 inhibition in HER2 positive breast cancers relative to the other subtypes. Through this initial exploration, CDK7 inhibitors have been found to show efficacy in multiple subtypes of breast cancer, including but without limitation to ER-positive, HER2-positive and TNBC, with no apparent selectivity to a particular subtype.

Disclosed methods include anti-proliferative treatment using CDK7 inhibitors alone as well as using CDK7 inhibitors in conjunction with other materials. For instance, in one embodiment a method is disclosed in which dual inhibition of EGFR and CDK7 can produce synergistic anti-proliferative effects on breast cancer cells across a broad spectrum of breast cancer subtypes.

Also disclosed are methods for determining response in any subtype of breast cancer to CDK7 inhibitors. In particular, it has been found that through determination of the basal expression level of CITED2 in a population or sample of breast cancer cells, information can be obtained with regard to the sensitivity of the breast cancer cells to CDK7 inhibition. Upon determination that the cancer cells are sensitive to CDK7 inhibition, targeted treatment of the cells (or a population or sample including the same cell type) via inhibition of CDK7 can prove efficacious in decreasing proliferation of the cancer cells, and this effect can be ubiquitous across all breast cancer subtypes.

Previous research has suggested that TNBC were uniquely dependent on CDK7 due to the inhibition of a cluster of TNBC-specific genes and that this dependence did not extend to ER-positive breast cancer cells. Bioinformatic analysis described further herein indicates, however, that CDK7 inhibition is associated with negative prognosis in all the major subtypes of breast cancer. As such CDK7 inhibition can be effective in multiple subtypes of breast cancers, and inhibitor sensitivity does not appear to correlate with effects on CDK7 expression or activity, cell cycle or apoptosis, or TNBC-specific gene expression.

While much of this discussion refers to the covalent CDK7 inhibitor THZ1, it should be understood that this disclosure is in no way limited to this particular CDK7 inhibitor, and any CDK7 inhibitor may show efficacy in decreasing proliferation of breast cancer cells. Selective CDK7 inhibitors can include, without limitation, THZ1 (see, e.g., Kwiatkowski et al. (2014); Nature 51 1 (751 1): 616-620), BS-181 (see, e.g., AN et al. (2009); Cancer Res 69(15): 6208-6215), SY-351 (Syros Pharmaceuticals) as well as those disclosed in US 2016/0264552, US 2017/0174692, US 2017/0183355, US 2016/0264554, and US 2016/0122323 (all of which are incorporated herein by reference), as well as any combination of CDK7 inhibitors.

A CDK7 inhibitor may be directly administered to a subject in need of treatment in an in vivo treatment or diagnostic protocol or the administration may be ex vivo administration to cells or tissue derived from a subject (for instance in diagnostics or study applications). For instance, a cancer cell population (also referred to herein as a cancer cell sample) can be directly contacted with the CDK7 inhibitor, i.e. the CDK7 inhibitor can be applied directly to a cell in an in vitro or ex vivo protocol), or alternatively the CDK7 inhibitor may be combined with the cell indirectly, e.g. by locating the CDK7 inhibitor in the bloodstream of a subject, which then can carry the CDK7 inhibitor to the cell in an in vivo treatment protocol. In one embodiment, a sample may be removed from a subject and tested ex viva for CITED2 expression levels, for instance in testing the cancer of a subject for sensitivity to a CDK7 inhibitor, as described further herein.

Methods of treating breast cancer according to the present disclosure can include administering to a subject a therapeutically effective amount of a CDK7 inhibitor. It should be understood that both human and veterinary uses are contemplated. In one embodiment, a CDK7 inhibitor can be administered in conjunction with one or more other anticancer or chemotherapeutic agents as are generally known in the art.

The CDK7 inhibitor may be delivered or administered acutely or chronically according to various delivery methods, including and without limitation sustained release methods, topical application (including dermal, transdermal, subcutaneous, etc.), parenteral (including, for example, intraarterial, intravenous, intramuscular, subcutaneous), osmotic pumps, inhalation, oral, nasal, mucosal (including sublingual), or intracavitary routes, and so forth.

The CDK7 inhibitor can be delivered in the form of a pharmaceutically acceptable composition that includes a suitable biologically acceptable carrier for the CDK7 inhibitor. A composition can be formulated in a variety of forms including solutions, suspensions, emulsions, and solid forms and are typically formulated so as to be suitable for the chosen route of administration, for example as capsules, tablets, caplets, elixirs for oral ingestion, in an aerosol form suitable for administration by inhalation (such as by intranasal inhalation or oral inhalation), ointment, cream, gel, jelly or lotion suitable for topical administration, or in an injectable formulation suitable for parenteral administration. The preferred route of administration will depend on a number of factors including the specific characteristics of the cancer to be treated and the desired outcome.

Beneficially, and regardless of subtype, breast cancer cell proliferation can be inhibited with low nanomolar concentrations of CDK7 inhibitor. For instance, in one embodiment a plurality of cells can be contacted with a CDK7 inhibitor at a concentration of about 500 nM or less, for instance from about 10 nM to about 400 nM, or from about 100 nM to about 250 nM, in some embodiments.

When considering indirect administration of a CDK7 inhibitor to a population of cancer cells, for instance for in vivo treatment of a cancer, the dosage amount can be determined such that an efficacious concentration of the CDK7 inhibitor contact the cancer cells. In one embodiment, a CDK7 inhibitor can be given in dosage generally varying from about 250 mg per day to about 3000 mg per day, for instance from about 500 mg per day to about 2000 mg per day up to about 2500 mg per day using various dosage regimens. The unit dosage strengths of the CDK7 inhibitor may be from about 100 mg to about 2000 mg or from about 250 mg to about 2000 mg, for instance from about 250 mg to about 1000 mg. Of course, dosage can vary as is known in the art, for instance based upon subject body weight, the specific state of the cancer, etc. For instance, a dosage amount for a patient can be from about 5 mg/kg/day to about 20 mg/kg/day, for instance about 10 mg/kg/day in one embodiment.

Methods for determining the sensitivity of a breast cancer cells to CDK7 inhibitors are also described herein. Determination of CDK7 sensitivity can be utilized in design of a treatment protocol for breast cancer treatment in a subject, e.g., in a personalized treatment protocol design. For example, in one embodiment, a treatment method can include initial determination of sensitivity to CDK7 inhibition for a particular cancer (e.g., through examination of an ex vivo sample of a cancer tumor) and then, upon determination that the cancer cells are sensitive to CDK7 inhibition, treatment can be carried out to decrease proliferation of the cancer cells, for instance via an in vivo treatment protocol.

As described further below, no correlation has been found between CDK7 RNA or protein levels and CDK7 inhibitor sensitivity. As such, further study has been carried out to determine if such correlation occurs with other biochemical compounds that could then provide a route for determination of efficacy of CDK7 inhibition therapy. Upon this further study, it has been found that THZ1 sensitivity correlates with the inhibition of several genes. In particular, a small set of genes have been identified that have been shown to be consistently decreased in cancer cell lines upon treatment with a CDK7 inhibitor. These genes include MYC, FOXC1, CDKN1B, PLK2, CITED2 and EGFR.

It has further been found that not only can CDK7 inhibitor inhibit CITED2 expression, but this gene, not previously associated with CDK7, can also show very strong association with THZ1 sensitivity. Specifically, a significant correlation has been shown to be present between the basal protein levels of CITED2 in cancer cells and sensitivity to CDK7 inhibitors. As such, in one embodiment, a method can include determining the sensitivity of breast cancer cells to targeted treatment with a CDK7 inhibitor by determining basal CITED2 expression level in a sample that includes the breast cancer cells.

CITED2 is a non-DNA binding transcriptional co-regulator that modulates the activity of multiple transcription factors including p300/CBP, Smad2/3 and estrogen receptor. CITED2 is overexpressed in breast cancer compared to normal mammary tissue and CITED2 has been associated with increased incidence of recurrence and breast cancer-specific death of breast cancer patients. High CITED2 mRNA expression has also been associated with poor survival in ER positive breast cancer patients and may contribute to anti-estrogen resistance. CITED2 also promotes proliferation, migration and resistance to chemotherapy in breast cancer.

A method for determining sensitivity of a cell population to a CDK7 inhibitor can include examination of the basal CITED2 expression level. The expression level for either CITED2 mRNA or CITED2 protein can be obtained, and any suitable method for determination of the expression level is encompassed herein and can include, without limitation, for proteins-immunohistochemistry (IHC) methods (combined with quantitative image analysis), Western blotting methods, ELISA methods, mass spectrometry approaches, etc.; and for nucleic acids-methylation analysis, quantitative RT-PCR, Northern blotting, real time PCR, etc. In general, for IHC methods, CITED2 positive cells will be more sensitive as compared to CITED2 negative cells.

Determination that the CITED2 expression level of a cancer cell sample is relatively high can indicate that the cells are sensitive to treatment by a CDK7 inhibitor. For example, in one embodiment the basal mRNA and/or protein CITED2 expression level of a sample of cancer cells can be compared to a basal CITED2 expression level for a breast cancer cell sample known to be resistant to (i.e., known to exhibit lesser sensitivity to) CDK7 inhibitors (e.g., BT474 and JIMT-1 breast cancer cell lines). Determination that the cancer cell sample expression level of CITED2 is higher than expected can indicate that the cells are sensitive to treatment by a CDK7 inhibitor.

In general, a basal CITED2 expression level of the tested cancer cell population that is about 1.5 times that of the comparison cells or greater, for instance about 2 times greater or even larger in some embodiments, can indicate that the cancer cell population is sensitive to treatment by use of a CDK7 inhibitor.

In one embodiment, a treatment method can include targeted treatment of a breast cancer cell population with a CDK7 inhibitor in conjunction with an EGFR inhibitor, which has been shown to provide a synergistic effect in decreasing proliferation of the targeted breast cancer cells.

Consistent with the effects of EGF stimulation on EGFR, PLK2, CDKN1B, FOXC1 and MYC, it has been found that EGF stimulation can result in a significant increase in CITED2 expression; an effect that can be inhibited by the addition of THZ1. These results indicate that both EGFR and CDK7 play a role in the regulation of CITED2 and suggest that targeting signaling activation via EGFR in combination with transcriptional activation via CDK7 can be a successful treatment strategy for breast cancer. In accord with this teaching, in one embodiment, breast cancer cells can be subjected to a combination treatment including both an EGFR inhibitor and a CDK7 inhibitor. Such a combination approach can result in additive or synergistic growth inhibitory effects.

In one embodiment, the EGFR inhibitor can be erlotinib hydrochloride (trade name Tarceva™), though the methods are not limited to utilization of any particular EGFR inhibitor. An EGFR inhibitor can include, for example, a small molecule inhibitor, an antibody or derivative or fragment thereof, or any other agent that targets the extracellular or intracellular domain of the EGFR. Combinations of EGFR inhibitors and types of EGFR inhibitors are also encompassed herein. In one embodiment, an EGFR inhibitor can be a tyrosine kinase inhibitor including, without limitation to, erlotinib, gefitinib, lapatinib, or any combination thereof. Antibody EGFR inhibitors can include, without limitation, cetuximab, panitumumab, or combination thereof.

In general, an EGFR inhibitor can be provided to a cancer cells at a concentration of about 500 nM or less, for instance from about 10 nM to about 400 nM, or from about 100 nM to about 250 nM, in some embodiments. When considering indirect administration of an EGFR inhibitor to cancer cells, for instance for in vivo treatment of a cancer, the dosage amount can be determined such that an efficacious concentration of the EGFR inhibitor contact the cancer cells. In one embodiment, an EGFR inhibitor can be given in dosage generally varying from about 250 mg per day to about 3000 mg per day, for instance from about 500 mg per day to about 2000 mg per day up to about 2500 mg per day. For instance, a dosage amount for a patient can be from about 5 mg/kg/day to about 20 mg/kg/day, for instance about 10 mg/kg/day in one embodiment.

A CDK7 inhibitor and an EGFR inhibitor can be delivered to cancer cells together in a single composition or separately, as desired. When delivered separately, the EGFR inhibitor-containing composition can be of the same type and using the same delivery mechanism as the composition containing the CDK7 inhibitor or different, as desired. Moreover, a composition containing one or both of a CDK7 inhibitor and an EGFR inhibitor can include carriers, solvents, and other additives as are generally known in the art.

Compositions for parenteral delivery, e.g., via injection, can include pharmaceutically acceptable aqueous and non-aqueous carriers, diluents, solvents or vehicles such as, without limitation, water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. In addition, a composition can contain minor amounts of auxiliary substances such as wetting or emulsifying agents, pH buffering agents and the like that can enhance the effectiveness of the miR-489. Compositions may also contain adjuvants such as preservatives, wetting agents, emulsifying agents and dispersing agents.

Prevention of the action of microorganisms may be ensured by the inclusion of various antibacterial and antifungal agents such as paraben, chlorobutanol, phenol, sorbic acid and the like. It may also be desirable to include isotonic agents such as sugars, sodium chloride and the like.

A composition can include one or more oil-soluble antioxidants including, without limitation, butylated hydroxytoluene (BHT), ascorbyl palmitate, butylated hydroxyanisole (BHA), α-tocopherol, phenyl-a-naphthylamine, hydroquinone, propyl gallate, nordihydroguiaretic acid, and mixtures thereof as well as any other known oil-soluble antioxidant compatible with the other components of the compositions. Mineral oils, animal oils, vegetable oils and silicones can be incorporated in a topical creams or lotions as disclosed herein. In addition to such oils, other emollients and surface active agents can be incorporated in an emulsion.

Thickeners such as natural gums and synthetic polymers, as well as preservatives such as methylparaben, butyl paraben, propylparaben and phenyoxyethanol, coloring agents and fragrances can be included in a composition, for instance a composition for topical application such as a lotion.

A composition may also contain, as optional additions, one or more soluble or dispersible pharmaceutically acceptable ingredients generally used in pharmaceutical emulsion compositions. Typical such ingredients include, for example, a preservative or antioxidant such as methyl or propyl paraben, butylated hydroxyanisole, imidazolidinyl urea and the like; a water or oil soluble vitamin such as vitamin C, tocopheryl linoleate and the like; and/or a colorant, odorant, humectant, thickener and the like.

Solid forms for oral administration may contain binders acceptable in human and veterinary pharmaceutical practice, sweeteners, disintegrating agents, diluents, flavorings, coating agents, preservatives, lubricants and/or time delay agents. Suitable binders include gum acacia, gelatin, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or calcium phosphate. Suitable flavoring agents include peppermint oil, oil of wintergreen, cherry, orange or raspberry flavoring. Suitable coating agents include polymers or copolymers of acrylic acid and/or methacrylic acid and/or their esters, waxes, fatty alcohols, shellac or gluten. Suitable preservatives include sodium benzoate, vitamin E, α-tocopherol, ascorbic acid, methyl paraben, propylparaben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene-sorbitan mono- or di-oleate, -stearate or -laurate and the like.

Emulsions for oral administration may further comprise one or more emulsifying agents. Suitable emulsifying agents include dispersing agents as exemplified above or natural gums such as guar gum, gum acacia or gum tragacanth.

Each additive of a composition may generally constitute between about 0.05% to about 15% of the total weight of the formulation. In one embodiment, a composition can include an additive in an amount between about 0.05% and about 10% or between about 0.05% and about 8%, or between about 0.05% and about 7%, or between about 0.05% and about 6%, or between about 0.05% and about 5% of the total weight of the formulation.

The present disclosure may be better understood with reference to the Examples set forth below.

EXAMPLE

Materials and Methods

Kaplan-Meier Plotter Online Survival Analysis

Kaplan Meier relapse-free survival curves for CDK7 (211297_s_at) were generated using www.kmplot.com from a total of 3,951 breast cancers (January 2017 dataset) of Affymetrix microarray data.

Cell Lines and Reagents

MDA-MB-468, MDA-MB-231, MCF7, T47D, BT474 and ZR-75-1 cells were from the American Type Culture Collection; all other cell lines were a gift from Dr. Norma O'Donovan (Dublin City University). MCF7 cells were maintained in DMEM-high glucose media (ThermoFisher Scientific) with 10% fetal bovine serum (FBS) (Atlanta Biologics), 1% penicillin-streptomycin and 2 mM L-glutamine (VWR), 1 mM sodium pyruvate (Sigma-Aldrich) and 5 mg insulin (Sigma-Aldrich). MDA-MB-468, MDA-MB-231, SKBR3 and JIMT-1 cells were maintained in DMEM-high glucose media (ThermoFisher Scientific) with 10% FBS, 1% penicillin-streptomycin and 2 mM L-glutamine. All other cell lines were maintained in RPMI-1640 (ThermoFisher Scientific) with 10% FBS, 1% penicillin-streptomycin and 2 mM L-glutamine. All cell lines were routinely confirmed to be free of Mycoplasma (MycoAlert PLUS mycoplasma detection kit (Lonza), and were authenticated by STR profiling by the University of Arizona Genetic Core or by Source Bio-science in 2016. THZ1 was purchased from MedChem as a 10 mM stock solution in DMSO.

Western Blotting

Cells were plated in 100 mm$^2$ petri dishes at a density of 1×10$^6$ cells/plate and allowed to grow for 3-4 days until the cells reached 80% confluency. Cells were treated with THZ1 or with vehicle control (DMSO) prior to lysing cells in RIPA buffer containing protease inhibitor cocktail and PMSF. Protein concentration was determined using BCA assay (Pierce). All lysates were prepared in biological duplicates. Protein (50 µg) was resolved on 4-20% Express-Plus PAGE gels in Tris-MOPS (SDS) running buffer (GenScript), transferred to PVDF membranes and incubated at 4° C. overnight with primary antibodies: CDK7 (sc-529, SantaCruz), ER (sc-543, SantaCruz), HER2 (#4290, Cell Signaling Technology), RNA-Pol II-S2P (C152000005, Diagenode), RNA-Pol II-S5P C152000007, RNA-Pol II-S7P (04-1570, Millipore) and RNA-Pol II (sc-900X, SantaCruz), CITED2 (MAB5005, R+D Systems), Tubulin (T-9026, Sigma), followed by anti-rabbit (#31460, ThermoFisher Scientific), anti-mouse (31430, ThermoFisher Scientific) or anti-rat (AP136P, Millipore) secondary antibodies. Bands were visualized with Western Lighting Plus ECL detection reagent (Perkin Elmer) using ChemiDoc Touch™ (BioRad). Images were analyzed and densitometry performed using ImageLab software (Biorad).

RNA Extraction, Reverse Transcription, and q-PCR

Cells were plated in 100 mm² petri dishes at a density of 1×10⁶ cells/plate and allowed to grow for 3-4 days until the cells reached 80% confluency. Cells were treated with THZ1 or with vehicle control (DMSO). Total RNA was extracted using RNAeasy Mini Kit (Qiagen) and 1 µg of total RNA was used to generate cDNA using iScript cDNA synthesis kit (BioRad). Gene expression was quantified using iTaq Universal SYBR green super mix on a CFX384 Real time system (BioRad). Primers used for real-time PCR are listed in Table 1, below.

TABLE 1

| Primer | Forward sequence | Reverse sequence |
| --- | --- | --- |
| CDK7 | TGAGAACATGGTAATGGGAGG (SEQ ID NO: 1) | ACAGTGCTCTGCCCTAAGTT (SEQ ID NO: 2) |
| ESR1 | CAGGATCTCTAGCCAGGCAC (SEQ ID NO: 3) | ATGATCAACTGGGCGAAGAG (SEQ ID NO: 4) |
| ERBB2 | GGTTCCTTCCCCTAATGGGTC (SEQ ID NO: 5) | CACCCCAAAGGCAAAAACG (SEQ ID NO: 6) |
| MYC | CCAACAGGAACTATGACCTCGACTAC (SEQ ID NO: 7) | CTCGAATTTCTTCCAGATATCCT (SEQ ID NO: 8) |
| PLK2 | TTGCGGCGTAGACTTTGTTA (SEQ ID NO: 9) | AGATCTCGCGGATTATCGTC (SEQ ID NO: 10) |
| CITED2 | CATATGGTCTGCCATTTCCA (SEQ ID NO: 11) | AAGGTCCCCTCTATGTGCTG (SEQ ID NO: 12) |
| EGFR | CTGACCAAAATCATCTGTGCCC (SEQ ID NO: 13) | CGTGGCTTCGTCTCGGAATT (SEQ ID NO: 14) |
| CDKN1B | ACAGAAGAAAATGTTTCAGACGGT (SEQ ID NO: 15) | CTTCTGAGGCCAGGCTTCTT (SEQ ID NO: 16) |
| SOX9 | GGAGAAACCGAGGTTGGAGG (SEQ ID NO: 17) | GGAGATAGCTTGTCCGGTGG (SEQ ID NO: 18) |
| STAT3 | CACCACAAGTCCCAGTAGGG (SEQ ID NO: 19) | GGAACCGACATTTGTTGGGC (SEQ ID NO: 20) |
| TRIB1 | TCAAGCAGATTGTCTCCGCC (SEQ ID NO: 21) | CAAAAGGCCACAGGAGAAGC (SEQ ID NO: 22) |
| RUNX1 | GGTGGGGATGGTTGGATCTG (SEQ ID NO: 23) | AACCCTGGTACATAGGCCAC (SEQ ID NO: 24) |
| IRS-1 | AAGGGGCAGCGTCACATAAA (SEQ ID NO: 25) | ACTACAACCCGCTCATGTCG (SEQ ID NO: 26) |

TABLE 1-continued

| Primer | Forward sequence | Reverse sequence |
| --- | --- | --- |
| BAMB1 | TTACAGAGGGCTGCACGATG (SEQ ID NO: 27) | GTCGTGGCTGTCACAAGTCT (SEQ ID NO: 28) |
| ELF3 | CCACCTGTGGGAGTTCATCC (SEQ ID NO: 29) | CATGTCCGGCTGTATCGTGA (SEQ ID NO: 30) |
| FADD | GCGTGGGTTTTCTCCGTACA (SEQ ID NO: 31) | CTCAGACAGCCGTGAAAAGC (SEQ ID NO: 32) |
| PIM3 | ACCGCGACATTAAGGACGAA (SEQ ID NO: 33) | GCGCTCACCGTCGAAGT (SEQ ID NO: 34) |
| NEDD9 | CTGTCCTCACGGGGGTTATC (SEQ ID NO: 35) | TCAAGGACTCAGGCTTGGAA (SEQ ID NO: 36) |
| DKK1 | TTCCTACTGTCTTCTCCTTCGT (SEQ ID NO: 37) | ATCCGGCAAGACAGACCTTC (SEQ ID NO: 38) |
| WEE1 | CGGTGAAAGCTTGGGGACTT (SEQ ID NO: 39) | TTGGGGACTATCACCACTTGC (SEQ ID NO: 40) |
| IL-8 | AAATTTGGGGTGGAAAGGTT (SEQ ID NO: 41) | TCCTGATTTCTGCAGCTCTGT (SEQ ID NO: 42) |

Cell Proliferation Assays

Cells were seeded in 12-well plates at densities ranging from 10000-30000 cells/well and after 24 hours cells were treated with 10, 40 and 100 nM THZ1 in triplicate. After 7 days the cells were imaged using Zeiss Axiovert 200 microscope using a 20× objective lens. Additionally, cells were plated in 96-well plates at a density of 2000 cells/well and after 24 hours treated with 0-10 µM THZ1. After 2 and 7 days the growth of the cells was measured by MTT assay.

Cell Cycle Analysis

MDA-MB-231 and T47D cells were seeded into 6-well plates and allow to grow until 60% confluent. The cells were then washed with PBS and the media was replaced with serum-free media overnight. After serum starvation the cells were treated with serum containing media in the presence or absence of 100 and 250 nM THZ1 for 24 and 48 hours. The cells were collected, fixed in ethanol overnight and cell cycle distribution was measured using DAPI on the LSR2 (Beckman-Dickinson).

EGF Stimulation

SKBR3 cells were seeded into duplicate 6-well plates and allowed to grow until 80% confluent. The cells were then washed with PBS and the media was replaced with serum-free media overnight. After serum starvation the cells were treated with 100 ng/ml EGF with or without 250 nM THZ1 for 6 hours then lysates were collected for both RNA and protein analysis.

Synergy Analysis

Cells were seeded into 96-well plates and after 24 hours plates were treated with THZ1 (0-50 nM), BS-181 (0-20 µM) and erlotinib or gefitinib (0-5 µM) alone or together in fixed ratio combinations. After 7 days, cell proliferation was measured by MTT assay.

Statistical Analysis

All results were presented as mean±standard deviation of 4-8 parallel assessments. Similar results were obtained from a minimum of two independent experiments. Statistical significance was tested using two-sided Student T-tests and populations were considered significantly different at $P<0.05$. Densitometry was performed on duplicate immunoblots using ImageLab software (Biorad) and normalized to tubulin loading controls and then correlated with the THZ1 IC50 values of each cell line. Statistical analyses were performed using SPSS 18.0 (SPSS Inc). Bi-variant scatter graphs and Spearman rank analyses were performed to evaluate associations between protein levels, mRNA and response to inhibition. IC50 values were calculated for MTT assays using CompuSyn software.

Results

Figure 1B:
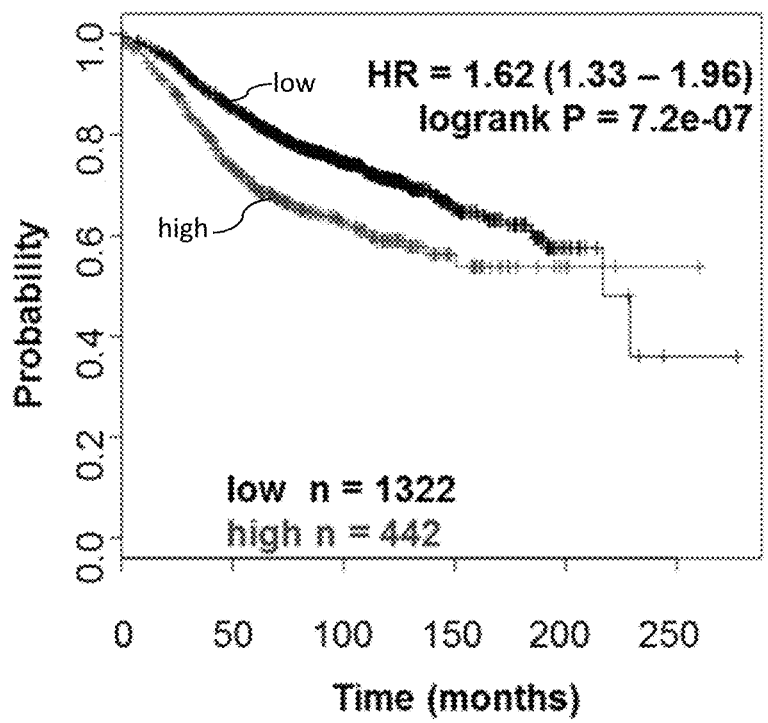
FIG. 1B illustrates the CDK7 expression data for Luminal A patients of the total sample set of FIG. 1A.
Figure 1C:
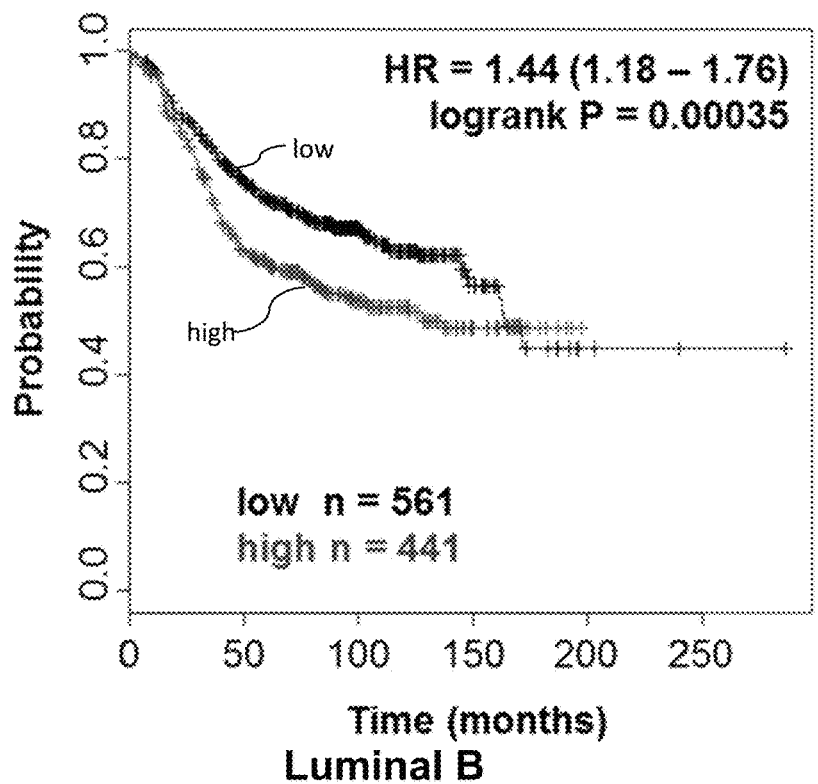
FIG. 1C illustrates the CDK7 expression data for Luminal B patients of the total sample set of FIG. 1A.
Figure 1D:
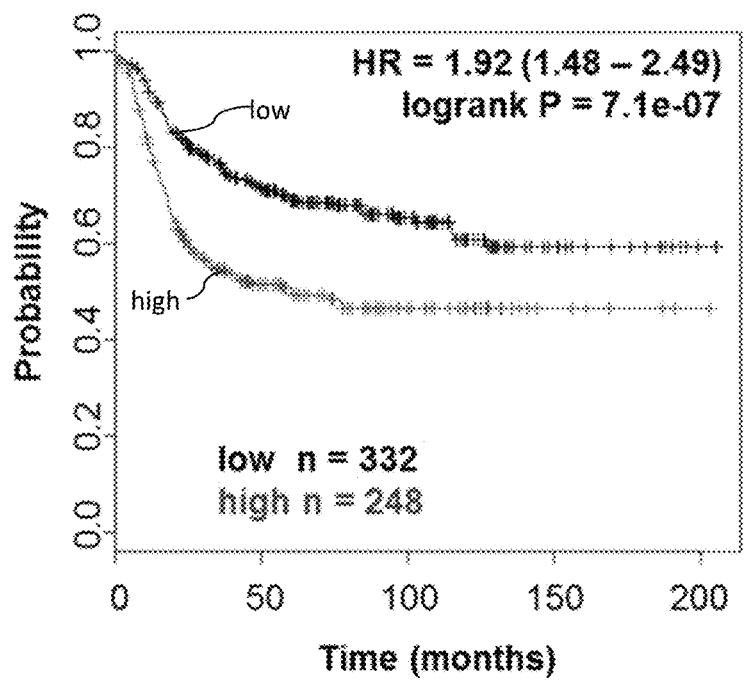
FIG. 1D illustrates the CDK7 expression data for Basal patients of the total sample set of FIG. 1A.
Figure 1E:
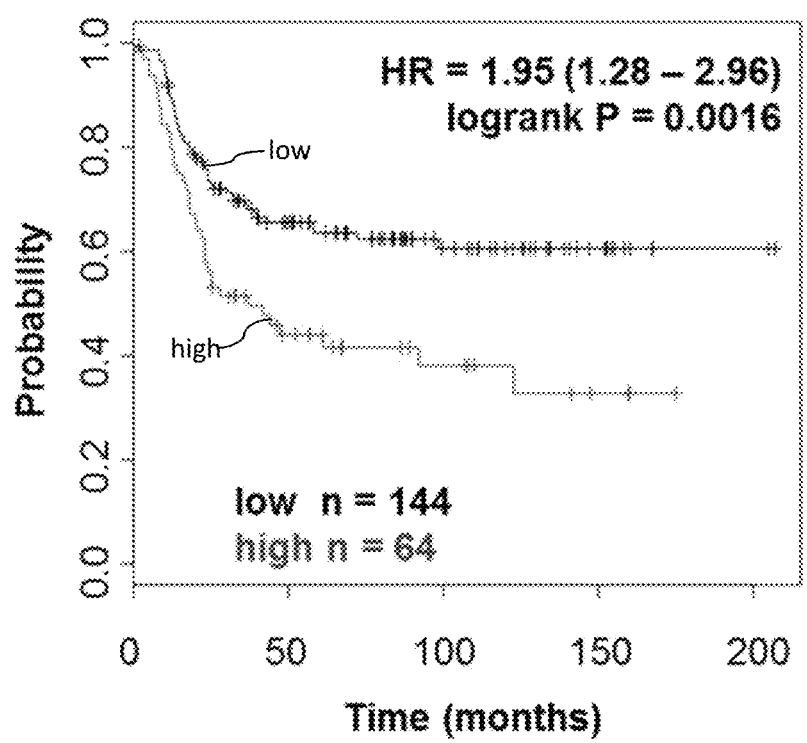
FIG. 1E illustrates the CDK7 expression data for HER2 positive patients of the total sample set of FIG. 1A.

High CDK7 Expression is Associated with Worse Relapse Free Survival in Breast Cancer Patients Correlations between CDK7 RNA expression and relapse-free survival (RFS) in breast cancer was investigated using a microarray database of 3,951 breast cancer patients (Gyorffy, et al., Breast Cancer Res Treat 2010; 123(3):725-31). Kaplan-Meier (KM) plots show that high CDK7 expression is associated with worse Relapse Free Survival (RFS) in an unselected cohort of breast cancer patients representing multiple different subtypes of breast cancer (p=2.4E-08, HR=1.43) (FIG. 1A). This analysis was then extended to examine correlations between CDK7 expression and RFS in the following breast cancer subtypes—Luminal A (FIG. 1B), Luminal B (FIG. 1C), Basal (FIG. 1D) and HER2 positive (FIG. 1E). In all analyses, high CDK7 expression correlated with worse RFS for patients regardless of subtype, with the strongest associations found in the luminal A (p=7.2E-07, HR=1.33) and in the basal (p=7.1-07, HR=1.92) subgroups. This suggested that CDK7 can be a target for breast cancer treatment beyond the triple negative subtype of breast cancer.

Breast Cancer Growth is Dependent on CDK7 Regardless of Subtype

Figure 2A:
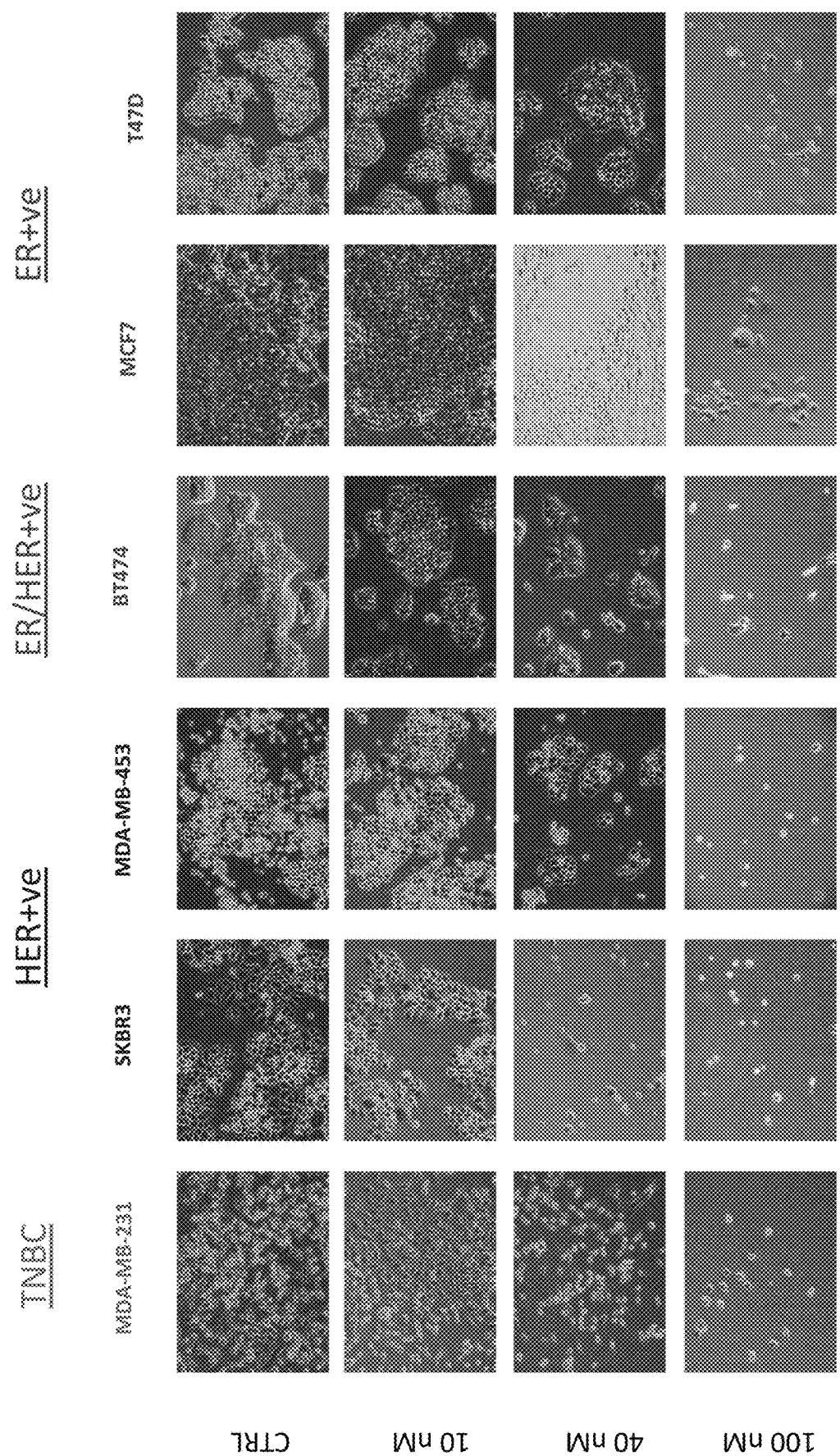
FIG. 2A shows bright-field images of various breast cancer cell lines treated with a vehicle control, 10 nM of THZ1 for 7 days, 40 nM of THZ1 for 7 days, or 100 nM of THZ1 for 7 days.

The effects of different concentrations of THZ1 on breast cancer cell lines was examined. Cell lines included TNBC, ER+HER2−, ER+HER2+ and ER−/HER2+ and effects were studied over seven days of treatment. While subtle differences in growth inhibition were observed at lower concentrations of THZ1, 100 nM THZ1 inhibited the growth of all tested cell lines regardless of subtype (FIG. 2A).

Figure 2B:
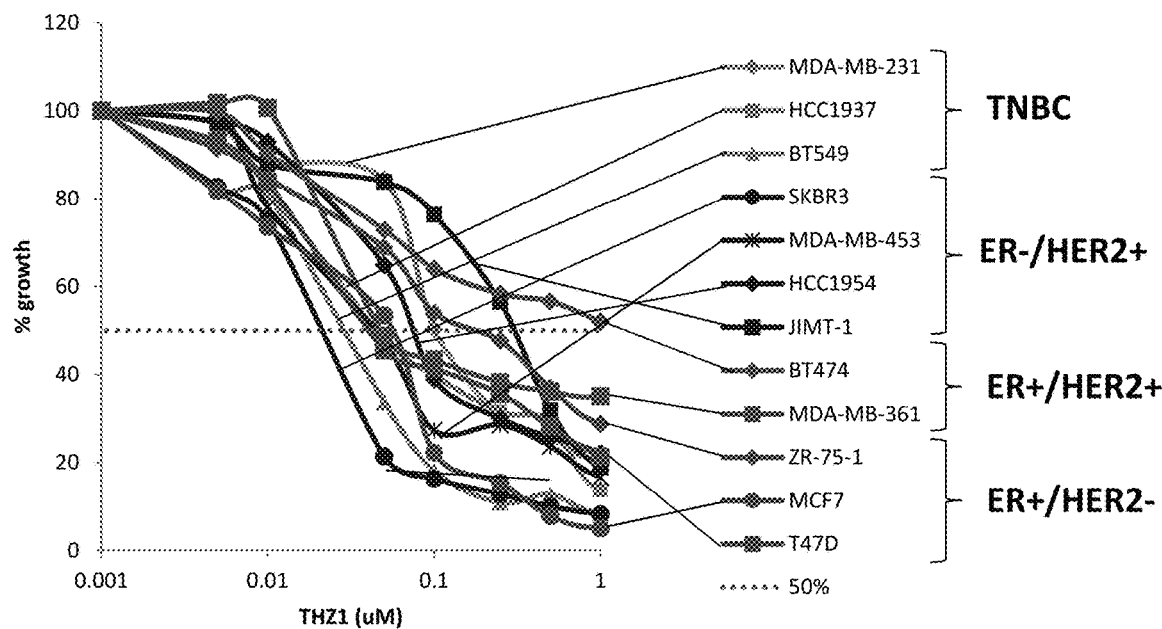
FIG. 2B shows the cell growth curves of TNBC, ER positive/HER2 negative, ER positive/HER2 positive, and ER negative/HER2 positive breast cancer cell lines treated with increasing concentrations of THZ1 for 2 days.

To investigate the effect of CDK7 inhibition in a time and dose dependent manner, an extended panel of 11 breast cancer cell lines were screened for response to THZ1 after 2 and 7 days of treatment. Two-day treatment with THZ1 with concentrations up to 1 µM significantly inhibited the cell growth, with most cell lines exhibiting IC50 values in the 100-300 nM range (FIG. 2B, Table 2, below).

TABLE 2

| Cell Line | 2 day IC50 (µM) | 7 day IC50 (µM) |
| --- | --- | --- |
| BT549 | 0.017 | 0.008 |
| SKBR3 | 0.023 | 0.009 |
| MCF7 | 0.032 | 0.059 |
| T47D | 0.089 | 0.014 |
| HCC1937 | 0.094 | 0.024 |
| MDA-MB-453 | 0.133 | 0.012 |
| MDA-MB-361 | 0.133 | 0.027 |
| HCC1954 | 0.158 | 0.036 |
| MDA-MB-231 | 0.159 | 0.036 |
| ZR-75-1 | 0.286 | 0.050 |
| JIMT-1 | 0.289 | 0.087 |
| BT474 | 0.490 | 0.027 |

Figure 2C:
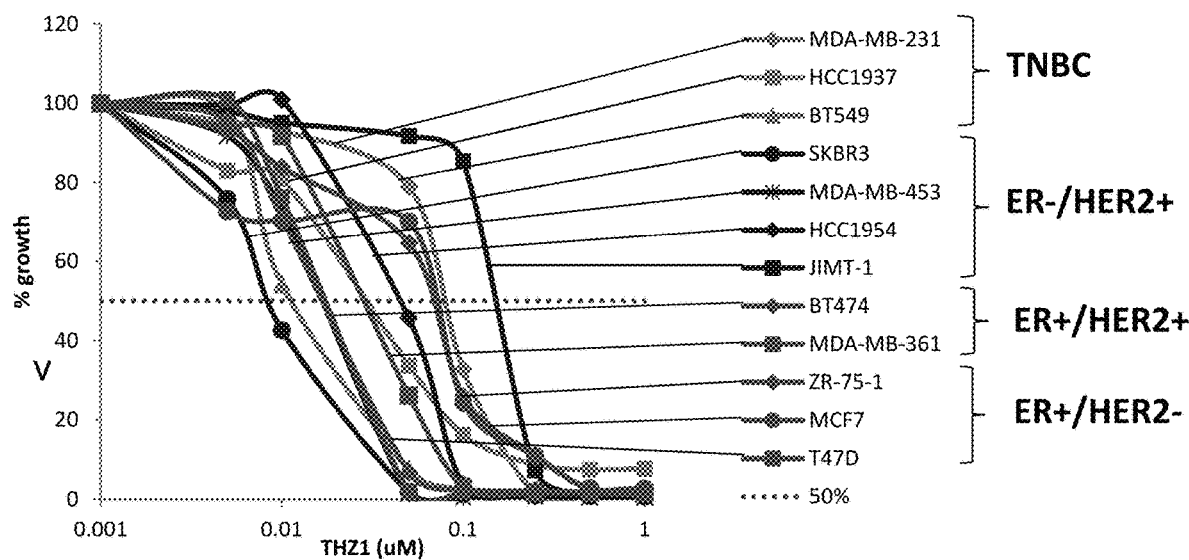
FIG. 2C shows the cell growth curves of TNBC, ER positive/HER2 negative ER positive/HER2 positive, and ER negative/HER2 positive breast cancer cell lines treated with increasing concentrations of THZ1 for 7 days.

However, when this analysis was extended to 7 days of the treatment, the only cell line exhibiting a lack of significant response to low nanomolar concentrations (<100 nM) was JIMT-1 (FIG. 2C, Table 2). There was a 25-fold difference in sensitivity determined by IC50 between the most sensitive cell line, SKBR3 and the least sensitive cell line JIMT-1.

Figure 8:
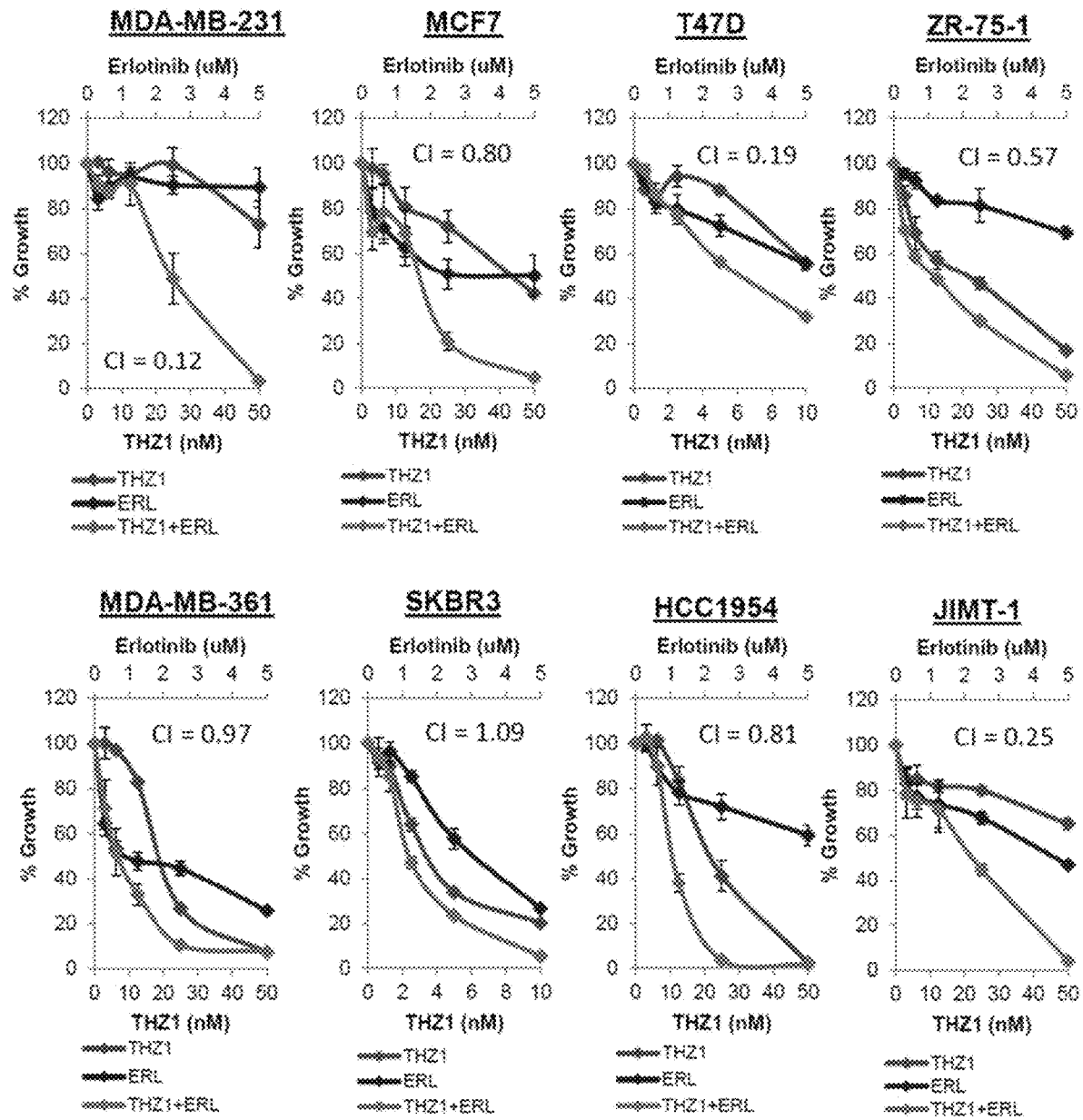
FIG. 8 includes graphs representing the dual inhibition of EGFR and CDK7 for various cell lines as labeled treated with low-dose THZ1 (0-50 nM) alone and in combination with erlotinib (0-5 µM) in fixed ratio combinations for 7 days.
Figure 9A:
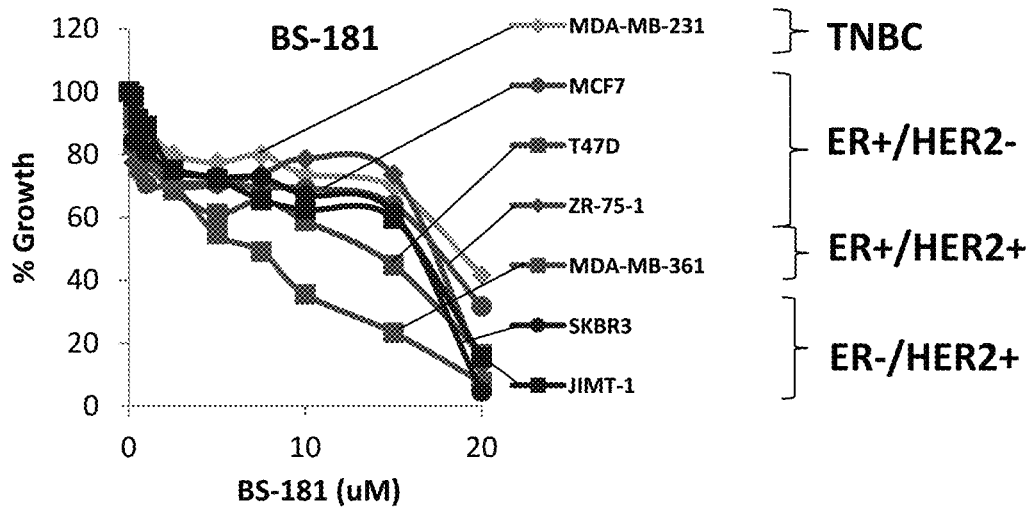
FIG. 9A shows the cell growth curves of TNBC, ER positive/HER2 negative, ER positive/HER2 positive, and ER negative/HER2 positive breast cancer cell lines treated with increasing concentrations of BS-181 for 7 days.
Figure 9B:
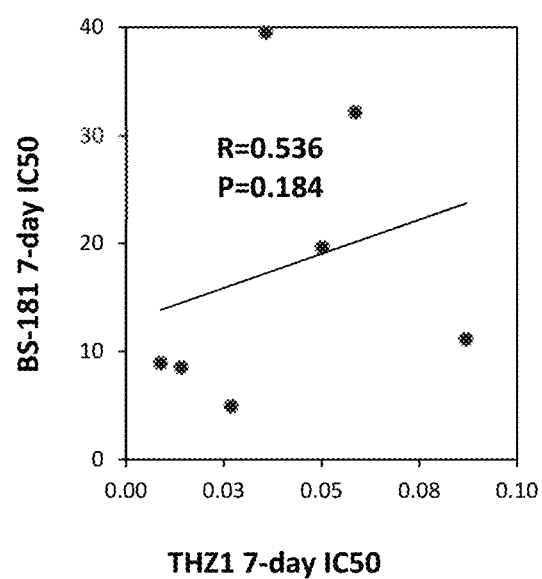
FIG. 9B illustrates a bi-variant scattergraph and Spearman rank correlation showing IC50 for BS-181 treated cells 7 days post-treatment compared to IC50 for THZ1 treated cells 7 days post-treatment.

The non-covalent CDK7 inhibitor BS-181 was also tested, which, like THZ1, also inhibited the growth of all tested breast cancer cell lines (FIG. 8A). While BS-181 was much less efficient than THZ1, there was a trend towards a positive correlation between IC50 values for THZ1 and BS-181 in the cell line panel (p=0.067) (FIG. 8B, Table 3, below).

TABLE 3

| Cell Line | 7 day IC50 (µM) |
| --- | --- |
| MDA-MB-361 | 4.9 |
| T47D | 8.5 |
| SKBR3 | 8.9 |
| JIMT-1 | 11.1 |
| ZR-75-1 | 19.6 |
| MCF7 | 32.1 |
| MDA-MB-231 | 39.5 |

CDK7, ER and HER2 Expression are not Predictive Biomarkers of THZ1 Response

Figure 3C:
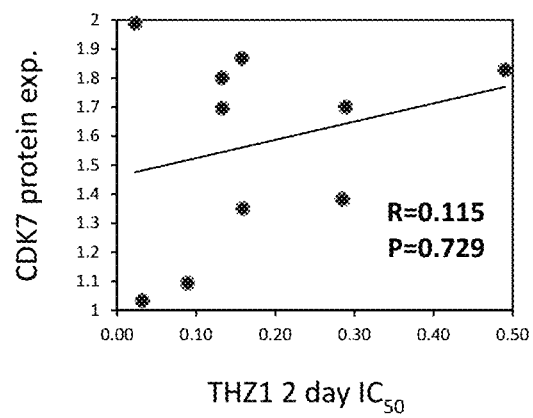
FIG. 3C shows bi-variant scattergraph and Spearman rank correlations showing CDK7 protein expression (relative to a control) vs. IC50 values at 2 days (top left) and at 7 days (top right) post-THZ1 treatment and CDK7 mRNA expression (relative to a control) vs. IC50 values at 2 days (bottom left) and at 7 days (bottom right) post-THZ1 treatment.
Figure 3C:
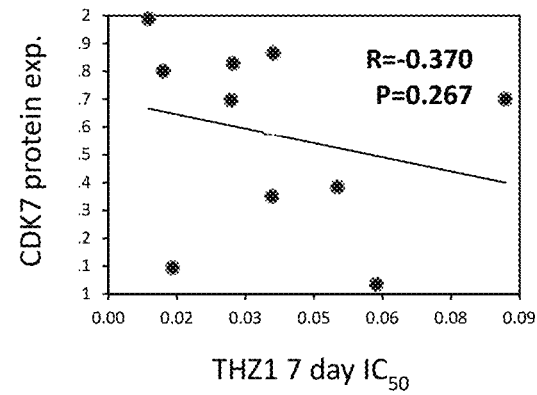
Figure 3C:
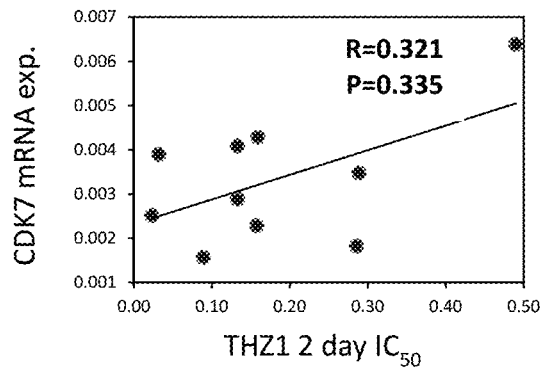
Figure 3C:
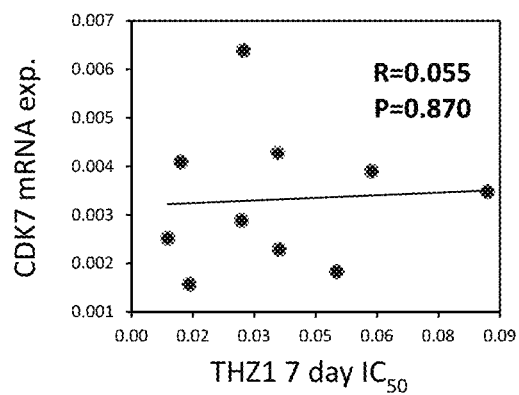
Figure 4A:
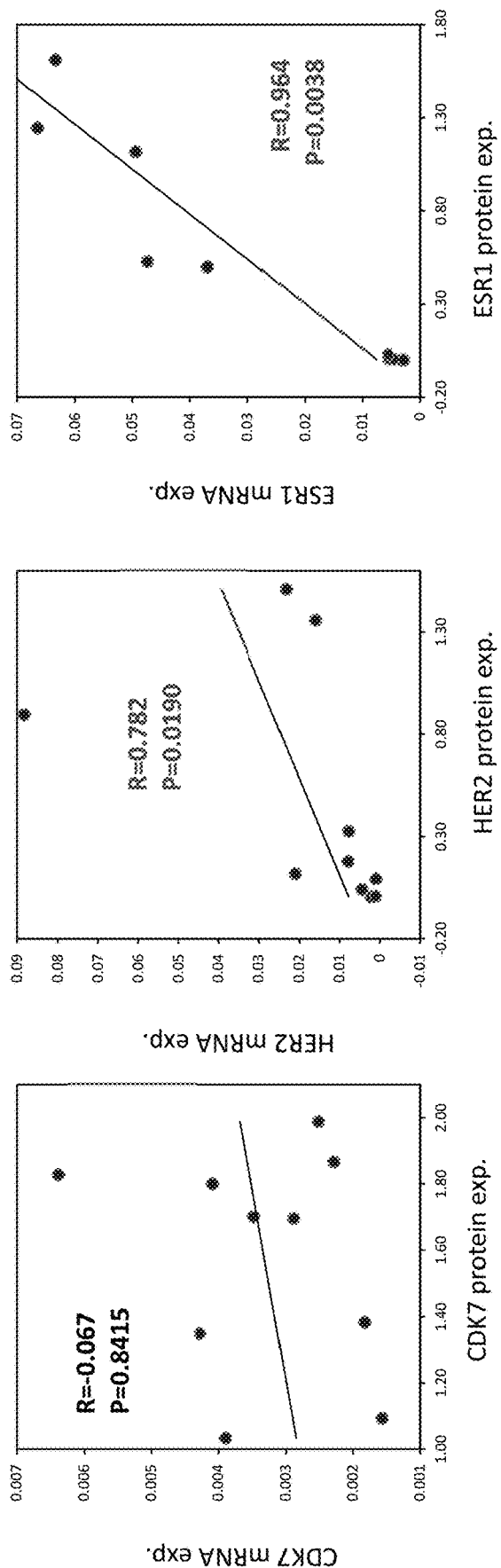
FIG. 4A provides bi-variant scattergraphs and Spearman rank correlations between the basal mRNA and protein expression levels of CDK7 (left), HER2 (center), and ER (right) across a cell line panel.
Figure 4B:
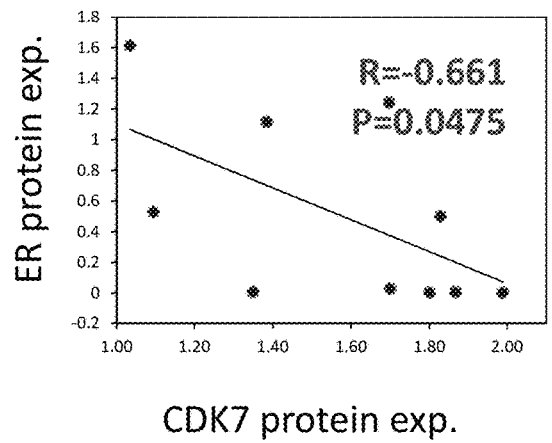
FIG. 4B provides bi-variant scattergraphs and Spearman rank correlations for CDK7 protein expression compared to protein expression of ER (top left), mRNA gene expression of ESR1 (top right), protein expression of ERBB2 (bottom left), and mRNA gene expression of ERBB2 (bottom right) across a cell line panel.
Figure 4B:
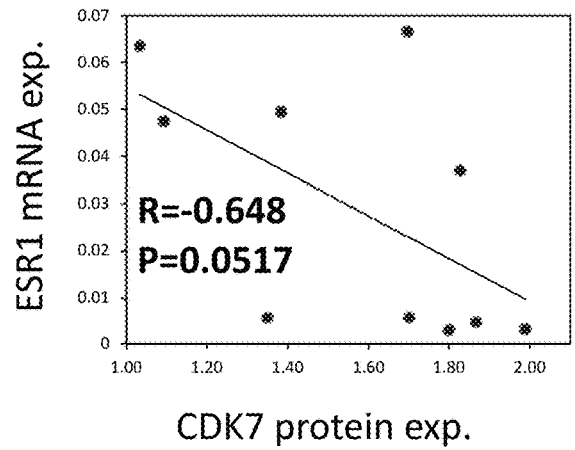
Figure 4B:
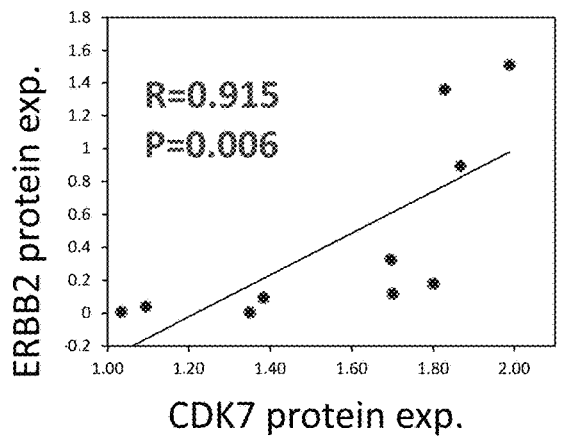
Figure 4B:
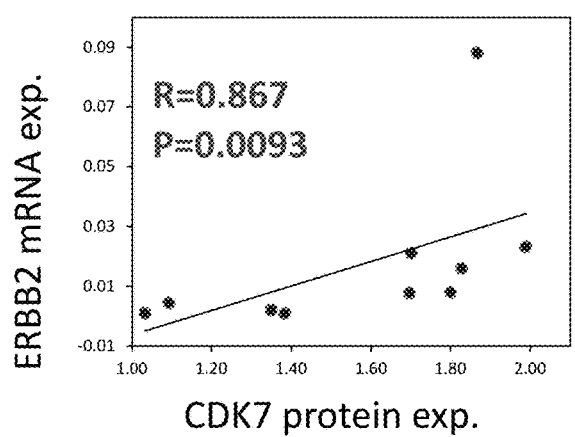
Figure 10:
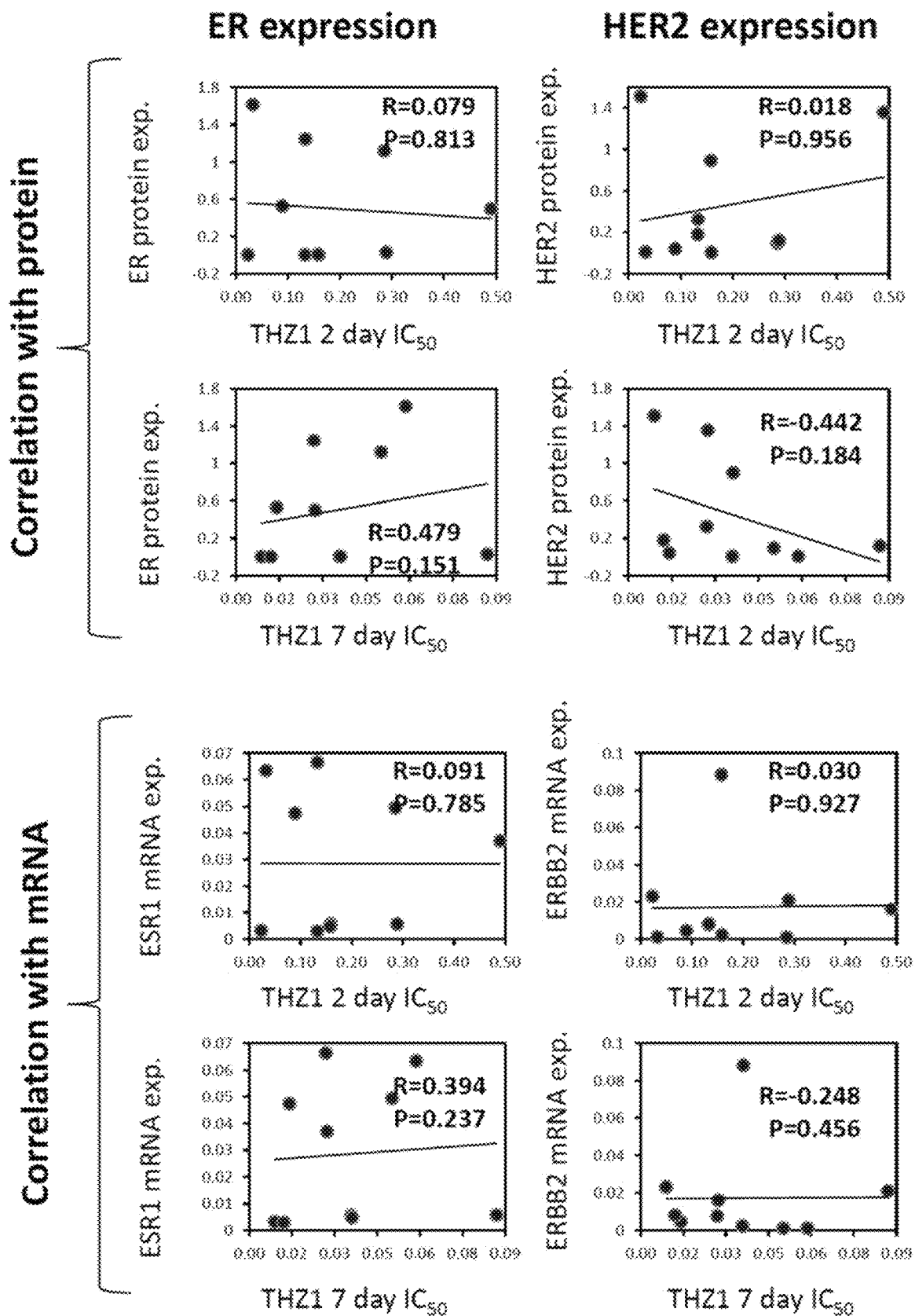
FIG. 10 provides bi-variant scattergraphs and Spearman rank correlations showing relative ER and HER2 protein expression levels (top) and mRNA expression levels (bottom) vs. IC50 values for THZ1 treated cells at 2-day and 7-day post-treatment across a cell line panel.

Determination was then sought as to whether CDK7 expression levels were predictive of response to CDK7 inhibition in the cell line panel. Both the protein and mRNA gene basal expression levels of CDK7 were measured, together with HER2 and ER (FIG. 3A, FIG. 3B). Neither mRNA nor protein basal levels of CDK7 correlated with response to THZ1 at either 2 days or 7 days of treatment (FIG. 3C). Surprisingly, there was no correlation between the mRNA and protein basal expression levels of CDK7 within the cell line panel; in contrast there was a strong positive correlation between HER2 mRNA and protein expression levels, and ERa (ESR1) mRNA and protein expression levels (FIG. 4A). A weak inverse correlation was found between the protein expression of CDK7 and the mRNA expression of ESR1 and a very strong positive correlation between CDK7 protein expression and HER2 at both the protein and mRNA expression level (FIG. 4B). However, the expression of HER2 or ER was also not predictive of response to CDK7 inhibition (FIG. 10). These results suggested that the expression of CDK7, HER2 and ER are not predictive of response to CDK7 inhibition.

Phenotypic Responses to CDK7 Inhibition

Figure 5A:
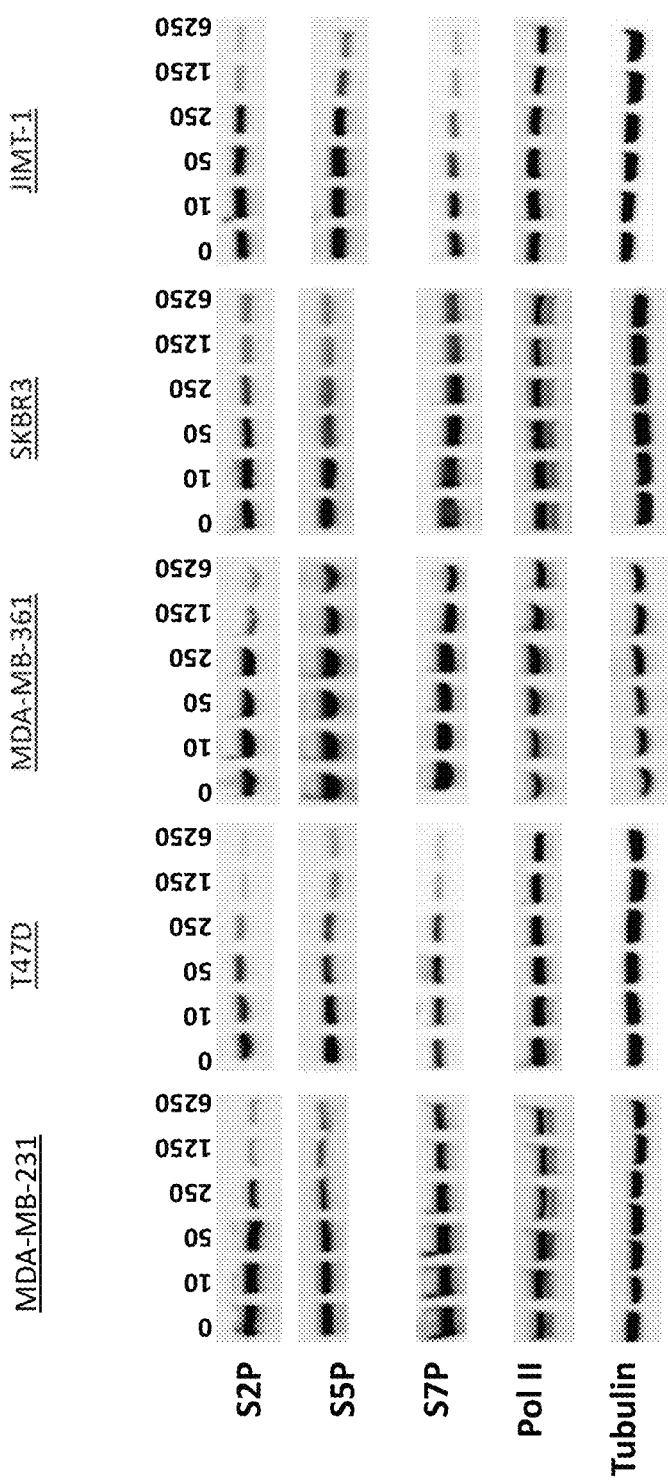
FIG. 5A illustrates immunoblotting results after cells were treated with a vehicle control (0) or increasing concentrations of THZ1 (10-6250 nM) for 4 hours, where immunoblotting was performed for RNA Pol II S2P, S5P, S7P and total Pol II with α-tubulin as a loading control.
Figure 11:
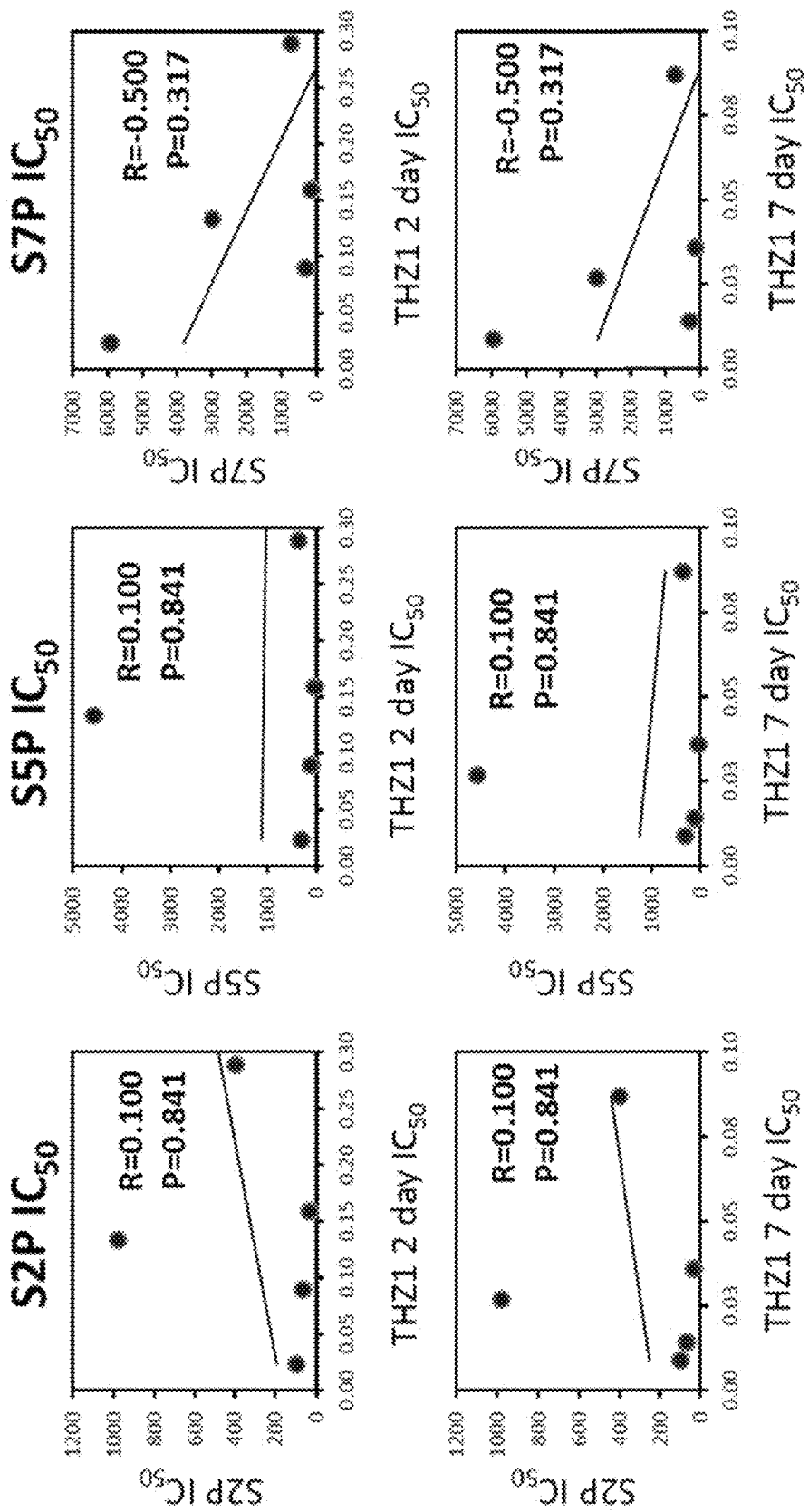
FIG. 11 provides bi-variant scattergraphs and Spearman rank correlations showing the results of densitometric analysis of RNA Pol II S2P (left), S5P (center), and S7P IC50 levels (right) vs. the concentration of THZ1 required to decrease the phosphorylation of each protein to 50% relative to control cells as expressed as an IC50 value, and providing potential correlations with sensitivity to THZ1 at 2 days and at 7 days.

CDK7 plays a key role in regulating the phosphorylation of RNA Pol II and THZ1 has previously been shown to inhibit the phosphorylation of RNA Pol II at S2, S5 and S7. The effects of increasing concentrations of THZ1 on the phosphorylation of RNA Pol II at S2, S5 and S7 was tested across multiple breast cancer cell lines. Results found that regardless of subtype, THZ1 inhibited the phosphorylation of all three sites in a dose dependent manner (FIG. 5A). The amount of THZ1 required to inhibit the phosphorylation to 50% of baseline levels was calculated for each cell line and compared to THZ1 growth inhibitory IC50 values. There was no correlation found (FIG. 11), indicating that the ability of THZ1 to inhibit CDK7 enzymatic activity does not correlate with its ability to inhibit cell growth.

Figure 5B:
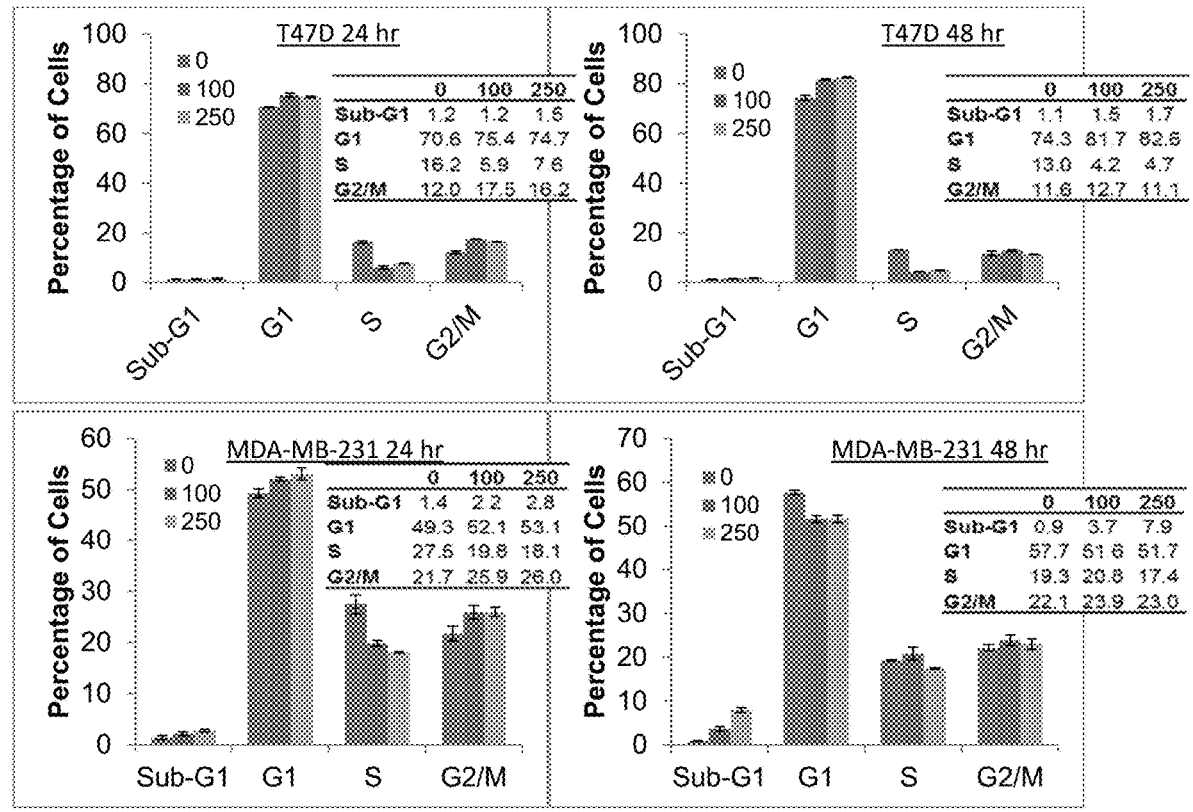
FIG. 5B provides graphs illustrating cell cycle distributions after THZ1 treatment including T47D cells treated with 0, 100 and 250 nM THZ1 with the cell cycle distribution profile analyzed after 24 hours (top left) and after 48 hours (top right); and MDA-MB-231 cells treated with 0, 100 and 250 nM THZ1 with the cell cycle distribution profile analyzed after 24 hours (bottom left) and after 48 hours (bottom right).
Figure 5C:
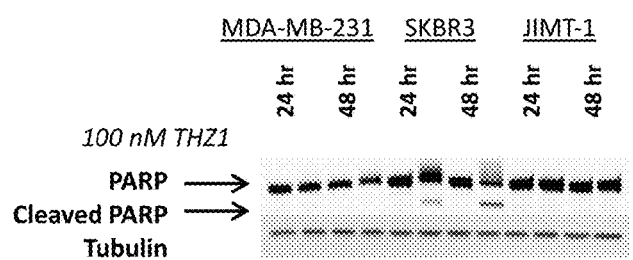
FIG. 5C illustrates immunoblotting results where MDA-MB-231, SKBR3 and JIMT-1 cells were treated with 250 nM THZ1 for 24 and 48 hours prior to immunoblotting analysis for PARP cleavage.

Previous reports have indicated that THZ1 acts as an inducer of apoptosis rather than cell cycle arrest in the TNBC cell line MDA-MB-468. Cell line analysis was performed on the TNBC cell line MDA-MB-231 and the ER positive cell line T47D and it was found that THZ1 treatment for 24 or 48 hours resulted in G1 arrest in T47D cells. MDA-MB-231 cells also responded with G1 arrest at 24 hours followed by increased sub-G1 (apoptotic cell) accumulation at 48 hours (FIG. 5B). PARP cleavage, another marker of apoptosis, in MDA-MB-231 was then compared to the most sensitive cell line, SKBR3 and the least sensitive cell line JIMT-1 and it was found that THZ1 induced PARP cleavage only in the SKBR3 cells (FIG. 5C). This suggested that THZ1 acts by inducing both G1 arrest and apoptosis in a cell line dependent manner.

Transcriptional Regulation by THZ1 in Breast Cancer

Figures 6A, 6B:
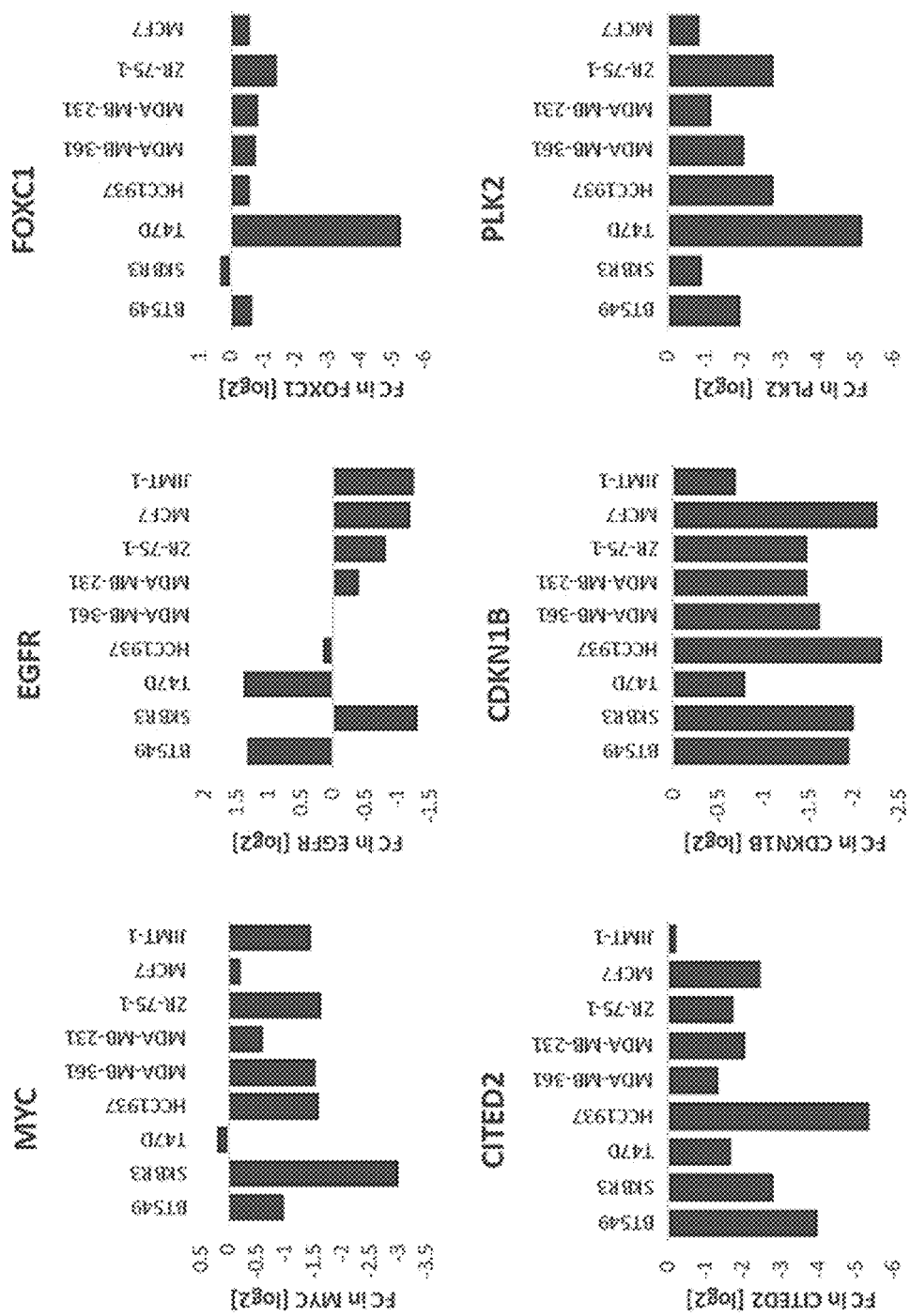
FIG. 6A shows results of qPCR analysis for the change in expression of MYC, EGFR, and FOXC1 following treatment of the breast cancer cell lines with 250 nM THZ1 for 6 hours prior to RNA extraction.
FIG. 6B shows results of qPCR analysis for the change in expression of CITED2, CDKN1B, and PLK2 following treatment of the breast cancer cell lines with 250 nM THZ1 for 6 hours prior to RNA extraction.
Figure 12:
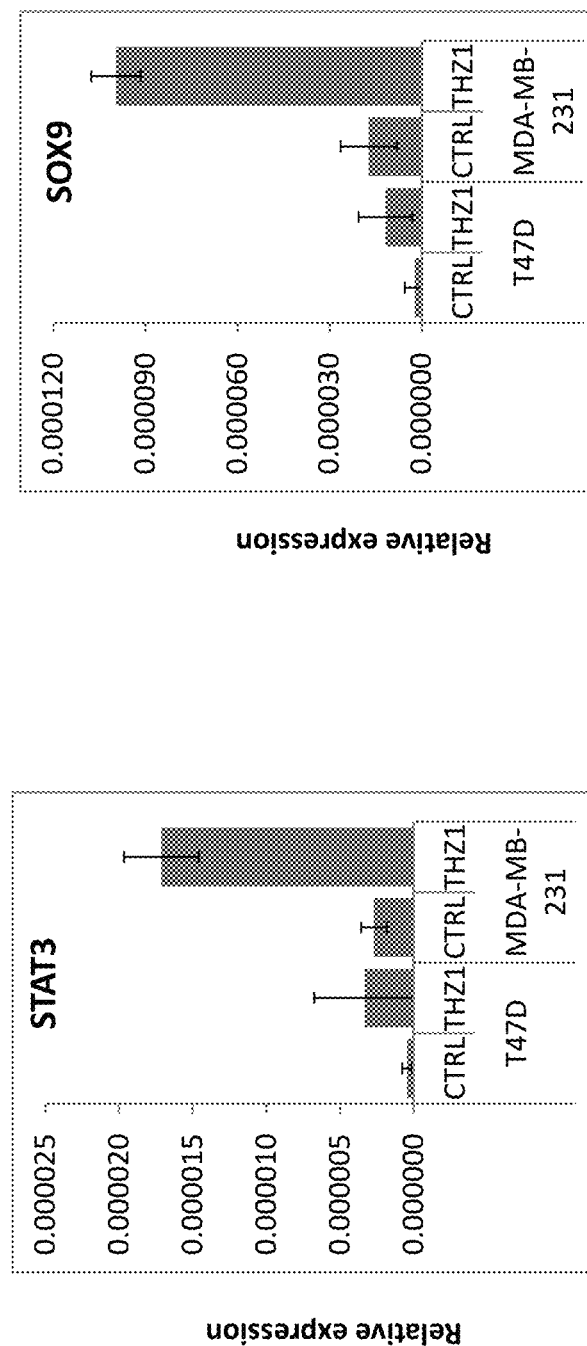
FIG. 12 illustrates the effect of THZ1 treatment on the expression of STAT3 and SOX 9; MDA-MB-231 and T47D cells were treated with 250 nM THZ1 for 6 hours prior to RNA extraction and qPCR analysis for the expression of STAT3 compared to vehicle treated cells is shown (left); MDA-MB-231 and T47D cells were treated with 250 nM THZ1 for 6 hours prior to RNA extraction and qPCR analysis for the expression of SOX9 compared to vehicle treated cells (right).

Previously published microarray data compared the effects of THZ1 treatment on two TNBC and two ER positive breast cancers to generate a subset of genes that were preferentially expressed in TNBC and inhibited by THZ1. This subset of genes included signaling molecules and transcription factors related to WNT, TGFB, STAT and EGFR/MET signaling including MYC, ETS1, SOX9, TWIST1 and FOXC1. Effects of THZ1 on several of these genes were examined and it was found that while some of the genes including SOX9 and STAT3 were not inhibited in response to THZ1 (FIG. 12), several genes including EGFR, MYC and FOXC1 were significantly inhibited by THZ1 in the majority of the cell lines tested, regardless of subtype (FIG. 6A). Re-analysis of a known microarray dataset of (Wang, et al. Cell 2015; 163(1):174-86) was carried out to select only for genes whose expression was altered greater than 2 fold by THZ1 in all 4 cell lines regardless of subtype. This analysis uncovered that only 5-6% of genes (1730/30724) were inhibited greater than 2 fold in all 4 tested cell lines. The top 20 genes ranked by largest fold change in gene expression in response to 250 nM THZ1 in MDA-MB-468 cells are shown in Table 4, below.

TABLE 4

| Gene Name | 468 FC | 549 FC | T47D FC | ZR751 FC |
|---|---|---|---|---|
| CYR61 | −4.82 | −2.96 | −1.96 | −1.81 |
| DKK1 | −4.7 | −5.01 | −1.09 | −4.15 |
| MYC | −4.64 | −3.06 | −2.68 | −2.98 |
| CITED2 | −4.53 | −4.12 | −2.71 | −2.64 |
| FBXO5 | −4.19 | −4.09 | −2.65 | −3.01 |
| CDKN1B | −4.11 | −3.06 | −2.3 | −2.57 |
| PIM3 | −4.05 | −2.73 | −2.54 | −3.96 |
| MARS2 | −4.04 | −3.73 | −2.3 | −3.75 |
| NEDD9 | −4.03 | −1.53 | −3.32 | −2.68 |
| E2F8 | −4.01 | −3.09 | −4.01 | −4.01 |
| PLK2 | −3.99 | −3.7 | −2.48 | −3.04 |
| FADD | −3.93 | −3.1 | −3.29 | −4.12 |
| ELF3 | −3.88 | −1.11 | −1.22 | −1.65 |
| MOCS3 | −3.84 | −4.2 | −3.86 | −4.1 |
| BAMBI | −3.8 | −2.97 | −1.74 | −3.77 |
| ZNF217 | −3.77 | −3.66 | −2.77 | −4.13 |
| PHLDA1 | −3.71 | −2.72 | −3.81 | −2.55 |
| TRIB1 | −3.69 | −4.07 | −2.31 | −3.54 |
| WEE1 | −3.69 | −2.95 | −1.96 | −3.25 |
| ZNF627 | −3.68 | −3.39 | −2.75 | −3.38 |

Figure 13:
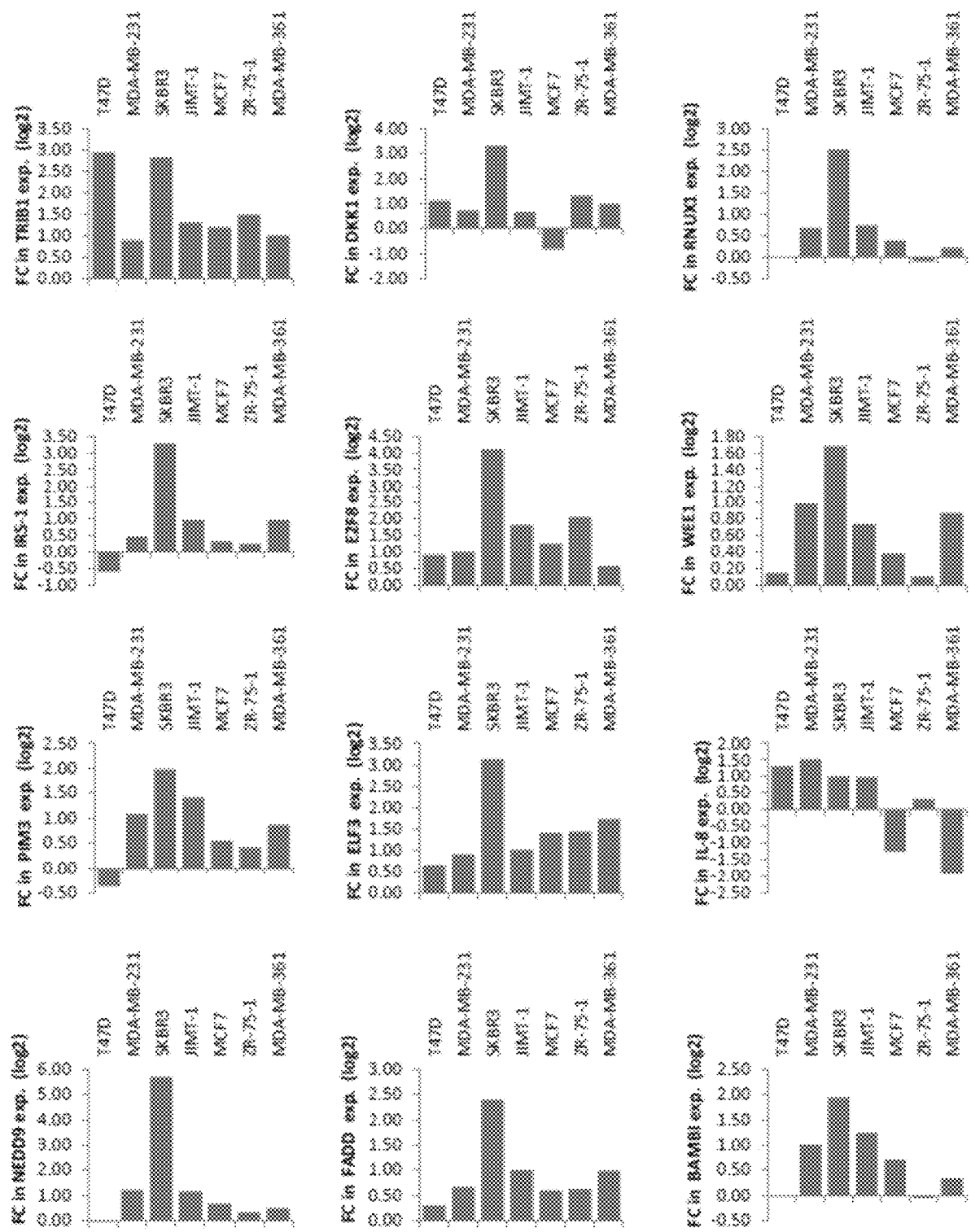
FIG. 13 shows fold change in gene expression for several genes of a panel of cells compared to vehicle treated cells following treatment with 250 nM THZ1 for 6 hours prior to RNA extraction and qPCR analysis. Genes examined include TRIB1, DKK1, RNUX1, IRS-1, E2F8, WEE1, PIM3, ELF3, IL-8, NEDD9, FADD, and BAMBI.

Many of these genes were found to be either unaltered or in some cases actually induced by THZ1 in the tested cell lines (FIG. 13). However, in addition to MYC, 3 genes (CITED2, CDKN1B and PLK2) were found to exhibit a significant decrease in expression following THZ1 treatment in the majority of tested cell lines (FIG. 6B). There was a significant positive correlation between the 2-day IC50 values for THZ1 across the panel and the fold change inhibition of CITED2 (p=0.037) and CDKN1B (p=0.028) (FIG. 5C). The same correlations were not found for 7-day THZ1 response.

The Role of CITED2 in Response to CDK7 Inhibition

The role that CITED2 plays in response to CDK7 inhibition was examined in more detail. In addition to the significant decrease in CITED2 mRNA expression in response to THZ1 in the cell line panel (FIG. 6B), it was found that the protein expression of CITED2 was also significantly decreased in response to CDK7 inhibition with THZ1 (FIG. 6D). It was then examined whether the basal mRNA expression of CITED2 could determine sensitivity to THZ1. CITED2 mRNA was detected in all cell lines, with the lowest expression found in BT474 and JIMT-1 cells. Higher basal CITED2 mRNA expression correlated with greater sensitivity to THZ1 at 2 days, with borderline significance (p=0.054). There were only 3 cell lines which exhibited high protein levels of CITED2, and basal CITED2 protein expression levels significantly correlated with sensitivity to THZ1 over 7 days (p=0.0385) (FIG. 6E). This suggested that CITED2 expression can be a predictive biomarker of response to THZ1 in breast cancer. The protein expression values provided on FIG. 6E were obtained from optical density measurements of the results of the western blotting assay relative to a control and represent the relative basal protein expression levels between all of the tested cell types.

Many of the genes that were significantly inhibited by THZ1 are EGF-regulated or have previously been reported to be altered by EGF stimulation or EGFR inhibition, including CITED2, which is a downstream target of MYC, which is in turn activated by EGFR signaling. Thus it was hypothesized that CITED2 may be regulated in both an EGFR and CDK7 dependent manner.

Figure 7A:
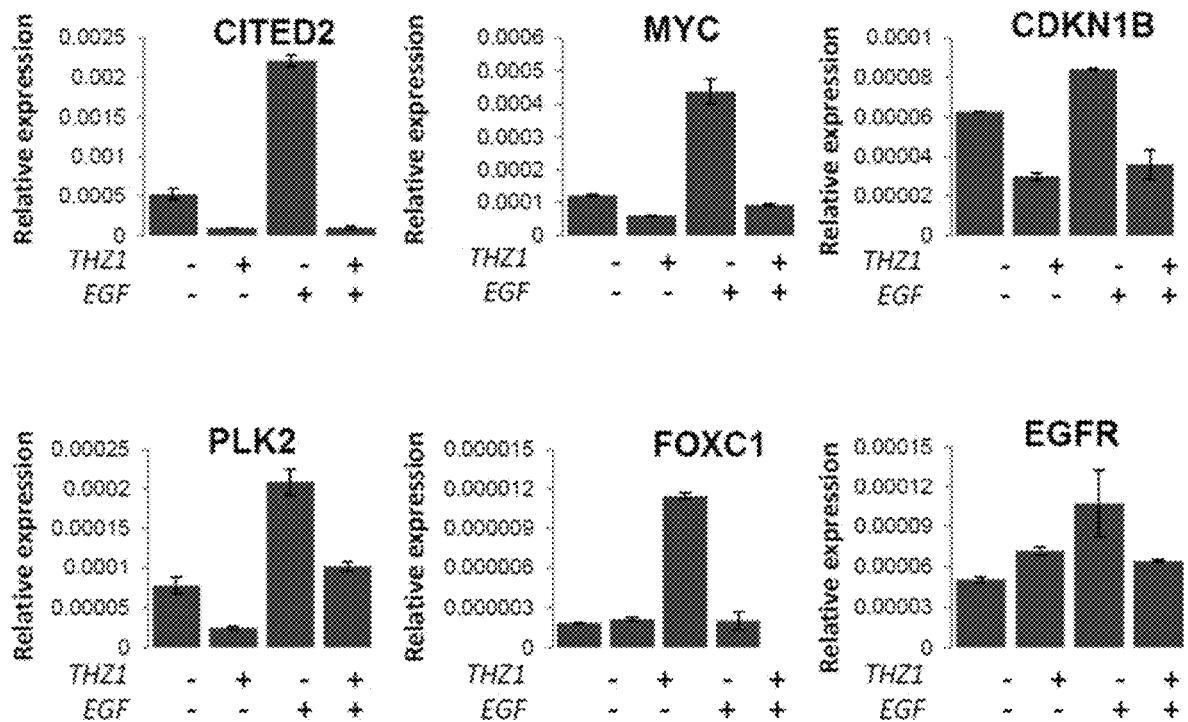
FIG. 7A shows relative mRNA expression levels (Q-PCR, as compared to a control) of CITED2, MYC, CDKN1B, PLK2, FOXC1, and EGFR for serum starved SKBR3 cells treated with 100 ng/ml EGF with and without 250 nM THZ1 for 6 hours.
Figure 7B:
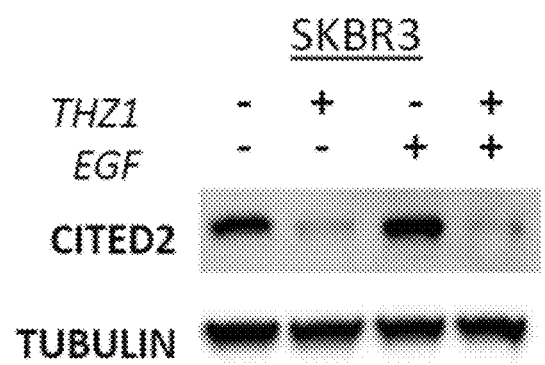
FIG. 7B illustrates the immunoblotting results for protein CITED2 levels of the cells with α-tubulin as a loading control.

Examination was carried out to determine if the expression of CITED2 was regulated by EGF. Treatment of serum starved SKBR3 cells with EGF resulted in a 4-fold increase in CITED2 expression and this induction was prevented by the addition of THZ1 (FIG. 7A). EGF stimulation also increased the expression of CITED2 protein and this increase was prevented by THZ1 treatment (FIG. 7B), suggesting that CITED2 expression is EGF and CDK7 dependent. EGF treatment also induced the mRNA expression of EGFR, MYC, CDKN1B, PLK2 and FOXC1 and this induction was also prevented by the addition of THZ1 (FIG. 7A).

Inhibition of CDK7 and EGFR in Breast Cancer

Having found that many of the genes inhibited by THZ1 are regulated in an EGF-dependent manner, it was hypothesized that inhibition of CDK7-mediated transcription via THZ1 could potentiate the effects of EGFR inhibition in breast cancer. To test this multiple cell lines were treated with low dose THZ1 in a fixed-ratio combination with the EGFR inhibitor erlotinib for 7 days. Synergy was analyzed using CompuSyn software that determines Combination Index (CI) values based on the drug combination principles of Chou-Talalay, providing a quantitative definition for additive effect (CI=1), synergism (CI<1), and antagonism (CI>1) in drug combinations. THZ1 synergized with erlotinib in the majority of tested cells lines (FIG. 8), with the most efficacious effect occurring in MDA-MB-231 cells (CI value of 0.12). The same combination treatment resulted in additive effects in SKBR3 and MDA-MB-361 cells. These results suggested that combining CDK7 and EGFR inhibition can be a therapeutic approach for the treatment of breast cancer.

While certain embodiments of the disclosed subject matter have been described using specific terms, such description is for illustrative purposes only, and it is to be understood that changes and variations may be made without departing from the spirit or scope of the subject matter.

What is claimed is:

1. A method for decreasing proliferation of breast cancer cells in a subject, comprising:
   determining an expression level of a CITED2 in a first sample of breast cancer cells that is an ex vivo sample of breast cancer cells obtained from the subject;
   comparing the expression level of the CITED2 in the first sample of breast cancer cells to the expression level of the CITED2 in a second sample of breast cancer cells that are known to be resistant to THZ1, wherein a determination that the CITED2 expression level of the first sample of breast cancer cells is greater than that of the second sample of breast cancer cells indicates that the breast cancer cells of the first sample are sensitive to the THZ1; and
   administering the THZ1 to the subject.

2. The method of claim 1, wherein the first sample of breast cancer cells comprise HER2 positive cells, ER positive cells, or TNBC cells.

3. The method of claim 1, wherein the CITED2 expression level of the first sample of breast cancer cells is about 1.5 times or greater than that of the second sample of breast cancer cells.

4. The method of claim 1, wherein the second sample of breast cancer cells comprises BT474 or JIMT-1 breast cancer cells.

5. The method of claim 1, wherein the CITED2 is CITED2 mRNA.

6. The method of claim 1, wherein the CITED2 is CITED2 protein.

7. The method of claim 1, further comprising administering an EGFR inhibitor to the subject.

8. The method of claim 7, wherein the EGFR inhibitor comprises a tyrosine kinase EGFR inhibitor.

9. The method of claim 8, wherein the tyrosine kinase EGFR inhibitor comprises erlotinib.

* * * * *